US011738175B2

(12) United States Patent
Vunjak-Novakovic et al.

(10) Patent No.: US 11,738,175 B2
(45) Date of Patent: Aug. 29, 2023

(54) METHOD AND APPARATUS FOR COMPUTER-VISION GUIDED TARGETED DELIVERY OF SMALL LIQUID VOLUMES INTO SELECTED LUNG REGIONS

(71) Applicant: The Trustees of Columbia University in the City of New York, New York, NY (US)

(72) Inventors: Gordana Vunjak-Novakovic, New York, NY (US); Jinho Kim, Jersey City, NJ (US); John O'Neill, New York, NY (US); Matthew Bacchetta, Tenafly, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 1001 days.

(21) Appl. No.: 16/546,620

(22) Filed: Aug. 21, 2019

(65) Prior Publication Data
US 2020/0046943 A1 Feb. 13, 2020

Related U.S. Application Data

(63) Continuation of application No. PCT/US2018/018649, filed on Feb. 19, 2018.
(Continued)

(51) Int. Cl.
*A61M 25/01* (2006.01)
*A61M 25/09* (2006.01)
(Continued)

(52) U.S. Cl.
CPC ......... *A61M 25/0147* (2013.01); *A61B 34/10* (2016.02); *A61B 34/20* (2016.02);
(Continued)

(58) Field of Classification Search
CPC ................................................. A61M 25/0147
(Continued)

(56) References Cited

U.S. PATENT DOCUMENTS

| 7,323,345 B1 * | 1/2008 | Stjernstrom | .......... B01L 3/5027 |
| | | | 436/179 |
| 8,052,621 B2 * | 11/2011 | Wallace | ............... A61B 5/6885 |
| | | | 600/587 |

(Continued)

FOREIGN PATENT DOCUMENTS

| WO | WO-2005058137 A2 * | 6/2005 | ......... A61B 1/00009 |
| WO | WO-2011140087 A2 * | 11/2011 | ..... A61B 17/320068 |

(Continued)

OTHER PUBLICATIONS

International Search Report cited in PCT/US18/18649 dated Nov. 6, 2018, 4 Pages.
(Continued)

*Primary Examiner* — Javid A Amini
(74) *Attorney, Agent, or Firm* — Reed Smith LLP; Lisa A. Chiarini; Walter M. Egbert, III

(57) ABSTRACT

The present invention relates to a computer-vision based autonomous steerable catheter device and methods of using the same for targeted delivery of a liquid microvolume into the interior of a lung.

9 Claims, 37 Drawing Sheets

Related U.S. Application Data

(60) Provisional application No. 62/512,441, filed on May 30, 2017, provisional application No. 62/462,011, filed on Feb. 22, 2017.

(51) Int. Cl.
*A61B 34/20* (2016.01)
*A61B 34/10* (2016.01)

(52) U.S. Cl.
CPC ... *A61M 25/0905* (2013.01); *A61B 2034/105* (2016.02); *A61M 2025/0161* (2013.01); *A61M 2025/0166* (2013.01); *A61M 2025/091* (2013.01)

(58) Field of Classification Search
USPC .......................................................... 604/19
See application file for complete search history.

(56) References Cited

U.S. PATENT DOCUMENTS

| | | | | |
|---|---|---|---|---|
| 2007/0197939 A1* | 8/2007 | Wallace | ................ | A61M 25/01 600/587 |
| 2008/0262422 A1* | 10/2008 | Cahill | ............... | A61M 25/0662 604/95.04 |
| 2010/0069921 A1* | 3/2010 | Miller | ................ | A61B 18/1233 600/301 |
| 2011/0066160 A1* | 3/2011 | Simaan | .................... | A61N 1/05 606/129 |
| 2014/0276612 A1* | 9/2014 | Sevensma | ......... | A61M 25/0136 604/95.04 |
| 2014/0296875 A1* | 10/2014 | Moll | .................. | A61M 25/0113 606/130 |
| 2017/0112571 A1* | 4/2017 | Thiel | .................. | A61B 18/1815 |

FOREIGN PATENT DOCUMENTS

WO    WO-2021127475 A1 *  6/2021  ......... A61B 1/00147
WO    WO-2021188757 A1 *  9/2021

OTHER PUBLICATIONS

Jinho Kim et al. Rapid Retraction of Microvolume Aqueous Plugs Traveling in a Wettable Capillary. Applied Physics Letters, 107(14):144101-144104, (2015).

Kim J, et al. Targeted delivery of liquid microvolumes into the lung. Proc Natl Acad Sci U S A. Sep. 15, 2015;112 (37):11530-5.

* cited by examiner

| Comparison of Human and rat lung models ||||
| Airway classification | Airway generation | Diameter (mm) ||
| | | Human (24) | Rat (26) |
| Proximal airway | 0-5 | 18-3.5 | 3.4-1.6 |
| | 6-15 | 2.8-0.66 | 1.34-0.36 |
| Distal airways | 16-23+ | 0.6-0.41 | 0.20-0.14 |

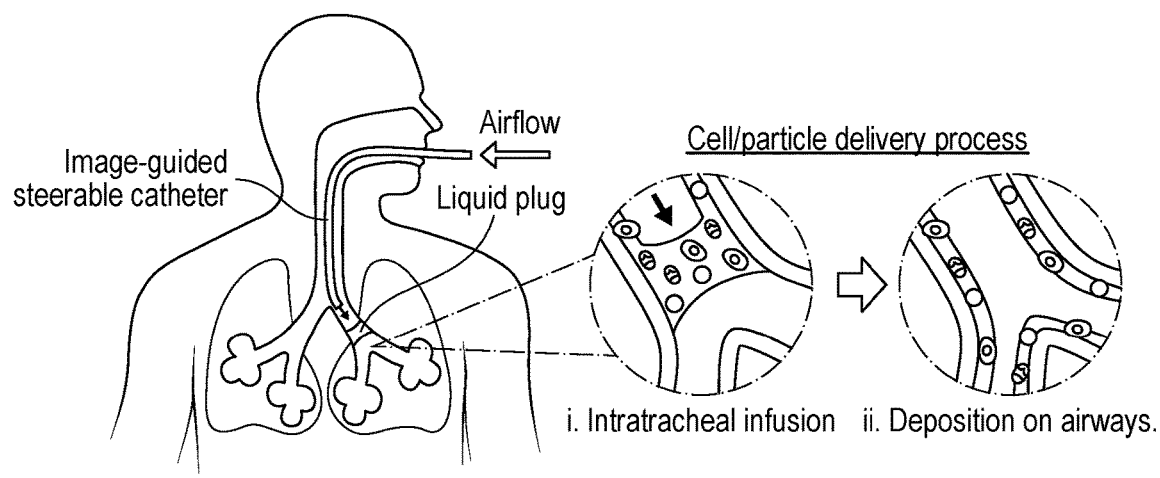
FIG. 14A
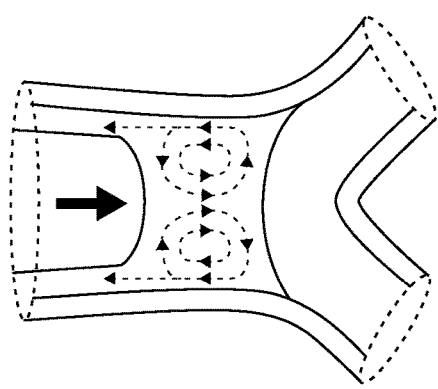 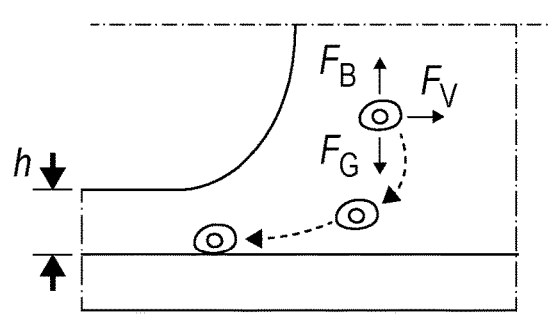
FIG. 14B  FIG. 14C

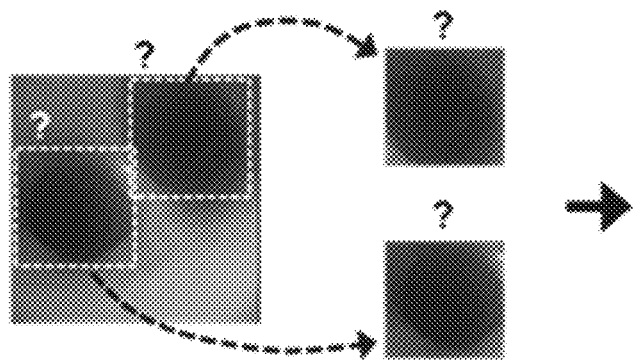
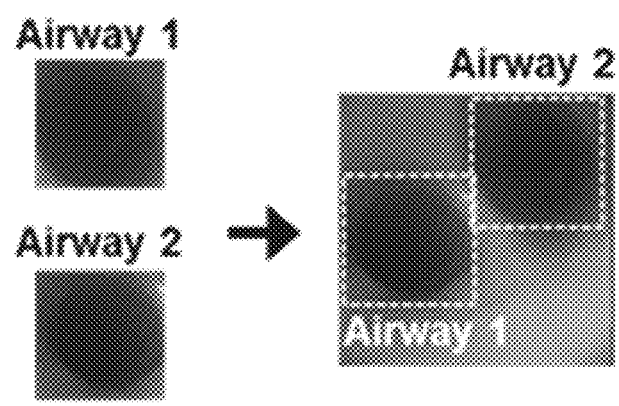
FIG. 25

METHOD AND APPARATUS FOR COMPUTER-VISION GUIDED TARGETED DELIVERY OF SMALL LIQUID VOLUMES INTO SELECTED LUNG REGIONS

CROSS-REFERENCE TO RELATED APPLICATIONS

The present application is a continuation of International Application No. PCT/US2018/018649, filed Feb. 19, 2018, which claims priority to U.S. Provisional Application 62/462,011, filed Feb. 22, 2017 and U.S. Provisional Application 62/512,441, filed May 30, 2017, the entirety of which are incorporated herein by reference.

FIELD

A method and apparatus configured for access to and targeted drug delivery to the lung.

BACKGROUND

Effective treatment strategies for lung diseases such as cystic fibrosis, tuberculosis, bronchopneumonia, and lung cancer would involve a small, highly concentrated dose of drug delivered directly to the pathologic site. Unfortunately, delivery of a precise drug dose to specific sites in the lung is challenging and often times not possible using conventional systemic drug administration methods, resulting in inefficient treatments for many lung diseases. Conventional technology available today is not designed to access remote parts of the lung. Therefore, there is no choice other than to administer drugs orally in hopes that the systemic distribution of the drug will treat the lung disease. Orally administered drugs often require high doses to achieve therapeutic effects due to first-pass metabolism, which in turn leads to systemic side effects. Although drugs administered intravenously can avoid first-pass metabolism, they can still incur a range of side effects.

On the other hand, inhalation of aerosolized drugs has the advantage of noninvasively bringing a drug locally into the lung, and so it has been a first-line treatment option for many lung diseases in the outpatient setting. In particular, dry powder inhalers can allow for local delivery of drugs in specific lung regions. Because properties of powders such as particle size, density, and cohesiveness strongly affect particle transport behavior, dry powders should be prepared with appropriate properties conducive to delivery into specific locations in the structurally complex pulmonary airway tree.

It is still desirable to find other, improved methods for delivering therapeutic agents to a targeted site in a lung.

In general, catheters are used in medical procedures in which tubular structures, lumens, pleural cavities or spaces of the body, such as airways, vessels, organs and joints, are diagnostically examined and/or therapeutically treated. Catheters, which can be introduced into the body through a natural orifice or through an incision, can deliver to the intended site within the body imaging devices, surgical instruments, implants, fluids, drugs, pharmacologic materials, biologic materials, biologic agents and therapeutics to treat or remedy various pathologies found therein.

SUMMARY

The present disclosure is directed to a steerable catheter device.

In one embodiment, the steerable catheter device comprises an elongate tubular member having a proximal section, distal section and an inner lumen defined there between, a plurality of guide members disposed circumferentially about the elongate tubular member in spaced apart arrangement extending from the proximal section of the elongate tubular member, a steering mechanism radially offset from the inner lumen, wherein the steering mechanism comprises two or more pulling wires arranged along the elongate tubular member length and independently passing through the plurality of guide members; and a controller disposed at an end of the proximate section of the elongate tubular member and operatively engaged to the steering mechanism, wherein the controller is adapted to selectively increase tension force independently to each of the pulling wires of the steering mechanism.

In another embodiment, the steerable catheter device comprises two, three or four pulling wires.

In another embodiment, the steerable catheter device comprises only two pulling wires.

In another embodiment, the steerable catheter device comprises three pulling wires arranged at angles of 120 degrees relative to each other around the elongate tubular member.

In another embodiment, the steerable catheter device comprises four pulling wires arranged at angles of 90 degrees relative to each other around the elongate tubular member.

In another embodiment, the steering mechanism of the steerable catheter device directs a distal tip of the distal section of the elongate tubular member to a desired locus.

In another embodiment, the controller of the steerable catheter device increases tension force to a first pulling wire while decreasing tension force or applying extension force to a second pulling wire to bend the elongate tubular member toward the first pulling wire.

In another embodiment, the controller of the steerable catheter device comprises a servo motor connected to each pulling wire to apply tension and extension forces to each pulling wire.

In another embodiment, the steerable catheter device further comprises an imaging system movably disposed in the inner lumen.

In another embodiment, the steerable catheter device further comprises at least one sensor to measure pressure, flow, oxygen, or carbon dioxide.

In another embodiment, the steerable catheter device further comprises a ventilator.

In another embodiment, the elongate tubular member of the steerable catheter device has an outer diameter that is less than 3 mm.

In another embodiment, the elongate tubular member of the steerable catheter device has an outer diameter that is less than 2 mm.

In another embodiment, the elongate tubular member of the steerable catheter device has an outer diameter that is 1.2 mm.

In another embodiment, the inner lumen of the steerable catheter device comprises a first lumen and a second lumen.

In another embodiment, the first lumen of the steerable catheter device contains a liquid and the second lumen contains an imaging probe.

In another embodiment, the steerable catheter device further comprises a computer-controlled robotic arm on which the elongate tubular member is supported.

In another embodiment, the steerable catheter device further comprises at least one servo motor operationally connected to the computer-controlled robotic arm.

In another embodiment, the computer-controlled robotic arm of the steerable catheter device facilitates movement of the distal section of the elongated tubular member.

In another embodiment, each of the plurality of guide members of the steerable catheter device is a guide-wire disk.

In another embodiment, the elongated tubular member of the steerable catheter device comprises a plurality of independently steered sub-elongated tubular members deployed from a main elongated tubular member.

In another embodiment, the sub-elongated tubular members of the steerable catheter device are autonomously steered.

The present disclosure is also directed to a method for targeted delivery of a liquid microvolume into a lung.

In one embodiment, the method for targeted delivery of a liquid microvolume into a lung comprises positioning a steerable catheter device into a pulmonary airway of a lung, steering the distal section of the elongated tubular member to position a distal tip proximal to a desired locus within the pulmonary airway, and instilling a liquid microvolume from the inner lumen of the elongated tubular member to an inner surface of the pulmonary airway.

In another embodiment, the step of steering the distal section of the elongated tubular member is facilitated by a computer-controlled robotic arm, wherein the computer-controlled robotic arm facilitates precise movement of the distal section of the elongated tubular member.

In another embodiment, the method for targeted delivery of a liquid microvolume into a lung further comprises forming a plug of the liquid across a diameter of the pulmonary airway; and transporting the plug distally through the airway with air pressure delivered from the inner lumen of the elongated tubular member, thereby depositing a film comprising a portion of the liquid microvolume behind the plug.

In another embodiment, the method for targeted delivery of a liquid microvolume into a lung further comprises forming a secondary plug at a bifurcation within the pulmonary airway.

In another embodiment, the method for targeted delivery of a liquid microvolume into a lung further comprises rupturing the plug by increasing air pressure delivered from the inner lumen of the elongated tubular member and extending the film of the liquid distally in the pulmonary airway.

In another embodiment, the method for targeted delivery of a liquid microvolume into a lung further comprises reforming the plug of the liquid by applying reduced air pressure from the inner lumen of the elongated tubular member.

In another embodiment, the liquid is transported to distal regions of the lung by repeated cycles of forming a plug of the liquid across a diameter of the pulmonary airway; transporting the plug distally through the airway with air pressure delivered from the inner lumen of the elongated tubular member; rupturing the plug by increasing air pressure delivered from the inner lumen of the elongated tubular member; and reforming the plug of the liquid by applying reduced air pressure from the inner lumen of the elongated tubular member.

In another embodiment, the liquid comprises a therapeutic agent.

In another embodiment, the elongated tubular member comprises a plurality of independently steered sub-elongated tubular members deployed from a main elongated tubular member.

In another embodiment, the sub-elongated tubular members are autonomously steered.

The present disclosure is also directed to a method of navigating a steerable catheter device.

In one embodiment, method of navigating a steerable catheter device comprises obtaining CT scan images of a lung having a target site; generating a three dimensional reconstructed airway model based on the CT scan images, thereby providing a navigation path to the target site; and maneuvering the device to enter a target airway, wherein the target airway is based on the navigation path provided by the three dimensional reconstructed airway model.

In another embodiment, the step of maneuvering the device is accomplished by an automated servo controller.

In another embodiment, the step of maneuvering the device is facilitated by a computer-controlled robotic arm, wherein the computer-controlled robotic arm facilitates movement of the distal section of the elongated tubular member.

In another embodiment, the method of navigating a steerable catheter device further comprises extracting a feature of an airway bifurcation in the three dimensional reconstructed airway model; and registering the feature with an image obtained in real-time during navigation of the device to the target site.

In another embodiment, the steps of extracting a feature and registering the feature identify the target airway for the device to enter at an airway bifurcation in the lung.

In another embodiment, the feature comprises geometrical shape, texture, or color of the airway bifurcation in the three dimensional reconstructed airway model.

In another embodiment, the step of extracting a feature is accomplished by using a feature detection algorithm.

In another embodiment, the step of extracting a feature is accomplished by using edge detection methods.

In another embodiment, the step of registering the feature is accomplished by using a feature matching algorithm.

In another embodiment, the method of navigating a steerable catheter device further comprises generating a training set of airway images from the three dimensional reconstructed airway model; developing an airway classifier for an airway bifurcation in the three dimensional reconstructed airway model; extracting an image of an unknown airway bifurcation during navigation of the device to the target site; and applying the airway classifier to the unknown airway bifurcation, thereby identifying the target airway to enter.

In another embodiment, the steps of generating a training set of airway images from the three dimensional reconstructed airway model; developing an airway classifier for an airway bifurcation in the three dimensional reconstructed airway model; extracting an image of an unknown airway bifurcation during navigation of the device to the target site; and applying the airway classifier to the unknown airway bifurcation, thereby identifying the target airway are done autonomously.

In another embodiment, the training set of airway images comprises images of an airway bifurcation from different viewing angles and distances in the three dimensional reconstructed airway model.

In another embodiment, the step of developing an airway classifier is accomplished by machine learning.

In another embodiment, machine learning comprises convolutional neural networks.

BRIEF DESCRIPTION OF THE DRAWINGS AND FIGURES

FIGS. 14A-14C show a schematic overview of cells and particulates deposited onto a tubular surface by liquid plug instillation.

FIG. 25 shows use of airway classifier on unknown airways using machine learning algorithms.

DETAILED DESCRIPTION OF THE DISCLOSED SUBJECT MATTER

Figure 1:
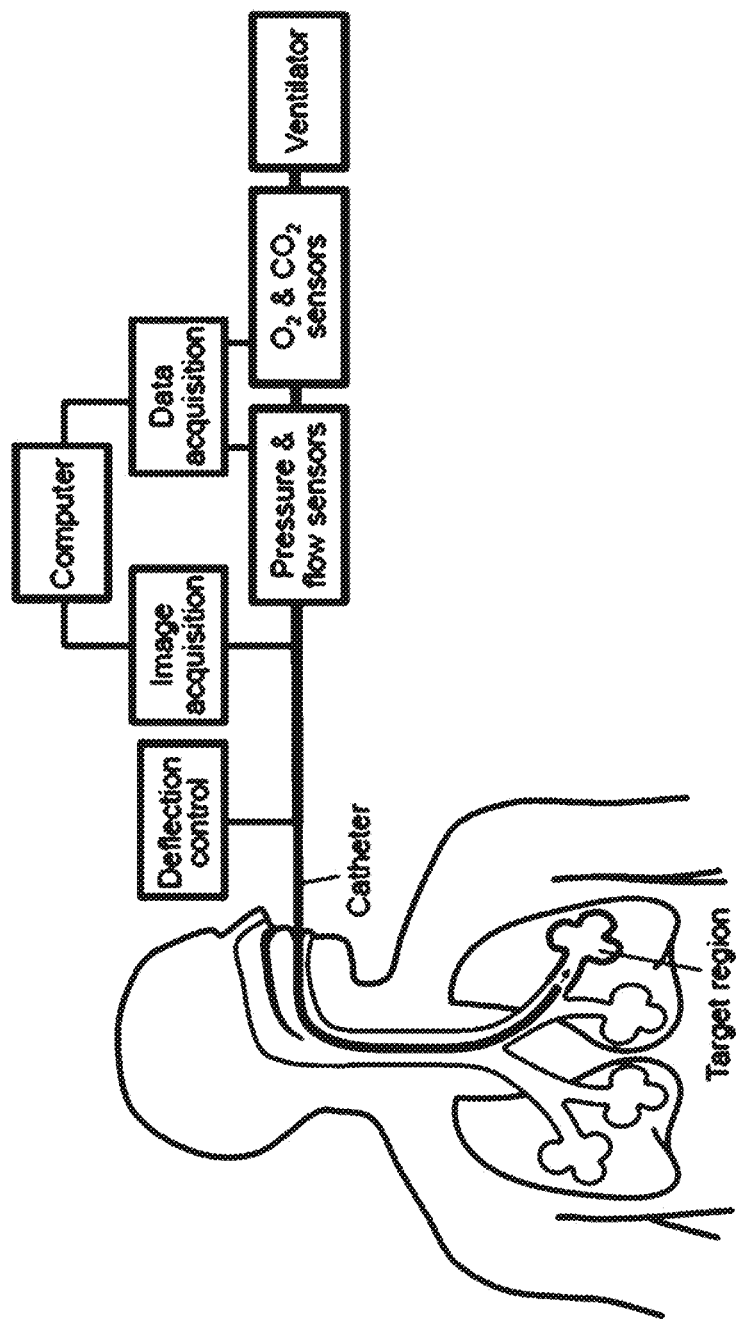
FIG. 1 is a schematic view of a steerable catheter system used for instillation of liquid into the lung of the patient.

While methods, systems and devices are described herein by way of examples and embodiments, those skilled in the art recognize that the methods, systems and devices for automated and targeted drug delivery in the lung are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to.

The basic components of one embodiment of a steerable catheter are described herein. As used in the description, the terms "top," "bottom," "above," "below," "over," "under," "above," "beneath," "on top," "underneath," "up," "down," "upper," "lower," "front," "rear," "back," "forward," "backward" and "left," "right" refer to the objects referenced when in the orientation illustrated in the drawings, which orientation is not necessary for using the devices or achieving the methods described herein.

The ability to deliver drugs to specific sites in the lung with high spatial precision could radically improve therapeutic outcomes of a variety of lung diseases, including cystic fibrosis, severe bronchopneumonia, chronic obstructive pulmonary disease, and lung cancer. Using conventional methods for pulmonary drug administration, precise, localized delivery of exact doses of drugs to target regions remains challenging.

Microvolumes of a liquid plug containing a therapeutic agent could be instilled into the lung using an airway catheter or bronchoscope, distributed across the airway epithelium, and absorbed locally. The therapeutic agent could be any number of reagents, for example a soluble reagent suspended in a liquid or particulates such as cells suspended in liquid. Although the plug instillation approach is rather invasive and more suitable for treatment in the inpatient setting, improved therapeutic effect could be achieved with minimal systemic absorption and more precise determination of the effective drug dose. Because a very small liquid volume is required in this process, potential flow-induced damage to delicate airway structures could be significantly reduced.

Described herein is a more controlled delivery of soluble reagents (e.g., drugs, enzymes, and radionuclides) in microvolume liquid plugs to targeted branches of the pulmonary airway tree, including upper airways, small airways (bronchioles), or the most distal alveoli. In this approach, a soluble liquid plug of very small volume (less than 1 mL) is instilled into the upper airways, and with programmed air ventilation of the lungs, the plug is pushed into a specific desired (more distal) airway to achieve deposition of liquid film onto the lung epithelium.

For delivery of the liquid microvolumes into the lung, it is desirable to use a lightweight, highly accurate, steerable catheter system where the catheter can be introduced into the body under direct and/or indirect visualization and is adapted to deliver the liquid to a target site in the lung.

In the human pulmonary airway there are normally 24 bifurcations or branches that divide the airway into various bronchi. A bronchopulmonary segment is a portion of a lung supplied by a specific tertiary bronchus (also called a segmental bronchus) and arteries. The segments are separated from each other by layers of connective tissue. Each bronchopulmonary segment is a discrete anatomical and functional unit. There are 10 bronchopulmonary segments in the right lung: three in the superior lobe, two in the middle lobe, and five in the inferior lobe. Some of the segments may fuse in the left lung to form usually 8-9 segments (4-5 in the upper lobe and 4-5 in the lower lobe). Lung segments can be further divided into subsegments, which are supplied by quaternary or smaller bronchi. Previous bronchoscopes and catheters have been unable to reach into the subsegmental portions of the lung due to their large size or insufficient flexibility and/or maneuverability to enter subsegmental portions of the airway. Described herein is a steerable catheter adapted to be positioned within a subsegmental portion of the pulmonary airway.

Desirably the steerable catheter has a distal end that is able to bend in as many degrees and planes as possible so that the catheter can be maneuvered through tight turns within the body, such as airway passages, vessel bifurcations, lumens, pleural cavities, and spaces within the tubular structures and capsular spaces of the body. It is also desirable that an imaging device is used to help steer the catheter, such as an image fiber or image sensor.

Described herein is such a steerable catheter system for use in delivering microvolumes of liquid into the lung, and more specifically into a subsegmental portion of the lung. The catheter system and methods for its use may be understood by reference to the Figures herein.

As shown schematically in FIG. 1, a steerable catheter described herein is used to deliver liquid into a target subsegmental region of the lung by insertion through the trachea of the patient into the pulmonary airway and ultimately into a subsegmental bronchus. The catheter comprises a deflection control system including a steering mechanism with associated controller and operating devices. It also may comprise imaging capabilities, including an imaging system and image acquisition software and hardware linked to a computer for controlling the imaging system and viewing and storing images. Other data may be acquired from various sensors including for example, measurements of pressure, flow, oxygen, and/or carbon dioxide. The data acquisition system may also be linked to a computer for analyzing and storage of the data. The catheter may also comprise a ventilator to provide air flow through the catheter to aspirate the lung through inspiration and expiration cycles described more fully below.

The steerable catheter can be maneuvered to a targeted site in a body cavity. Notably, as shown in FIG. 1, the catheter can be introduced into the pulmonary airway of a lung through the trachea and through branches in the airway to a target region or site in the more distal subsegmental regions of the airway. Accordingly, provided is a method of orienting a catheter device, as described above including any embodiments, within a bodily cavity, the method comprising: positioning the catheter within a bodily cavity, and increasing tension force to a first one of said pulling wires while decreasing tension force or applying extension force to a second one of said pulling wires to bend said catheter body toward the first pulling wire. Preferably, the method comprises applying extension force to the second pulling wire.

As can be seen in FIGS. 2A-2D, the catheter body has a generally cylindrical body that is shown in particular as a tubular member with an inner lumen. The cylindrical body has a longitudinal axis along which the length of the cylindrical body is defined. As shown in schematic and photographic image in FIG. 2A, extending through substantially the entire length of the catheter body are two or more pulling wires arranged along the length of the elongate tubular member passing through wire guide members. As shown in FIG. 2A, the pulling wires extend from the proximal end of the catheter through the elongated catheter body to an endpoint near the distal end. In particular, as shown in a schematic cross section in FIG. 2C, two pulling wires are shown passing through holes integrally formed in a guide member (wire guide disk) surrounding a tubular member surrounding the inner lumen, illustrated in FIG. 2C as a dual lumen. Each pulling wire is shown radially offset from the inner lumen. Equal tension on both pulling wires (or all wires, if the catheter comprises more than two pulling wires) will keep the catheter distal section in a straight original shape. FIG. 2D shows a plan view of the distal section of the catheter contiguous to the distal end of the proximal section of the catheter. Line A-A shows the axis of orientation for the cross section and plan views of the catheter. The proximal section of the catheter comprises a flexible outer sheath with an outer diameter similar or equal to the outer diameter of the guide members and an inner diameter equal to or greater than the outer diameter of the inner lumen. As shown in FIGS. 2B and 2D, the steering mechanism can cause the distal section to bend into a deflected shape. Applying increased tension force to a first one of said pulling wires while decreasing tension force or applying extension force to a second one of said pulling wires will result in bending the distal section of the catheter body toward the first pulling wire. A condition where an extension force is applied to the second pulling wire is shown in these views.

As depicted in FIG. 2C, the two pulling wires are shown in diametrically opposed arrangement, i.e. in upper and lower regions of the cross section of the catheter body. Although illustrated in FIG. 2C with two pulling wires, the catheter may comprise two or more pulling wires such as two, three or four pulling wires preferentially arranged symmetrically around the circumference of the tubular body and through the guide members. When the catheter comprises three pulling wires, they are preferentially arranged at angles of 120° relative to each other around the tubular body. Four wires are preferentially arranged at angles of 90° relative to each other around the tubular body. Three or four wires may allow for greater maneuverability of the tip of the catheter through a narrow curving pathway, such as through a pulmonary airway. When a combination of tension force is applied to at least one pulling wire and either decreased tension or extension force is applied to at least one pulling wire generally opposed across the tubular body from the first, the distal section will deflect toward the pulling wire(s) under tension.

The catheter body is made of a highly elastic material with a low modulus of elasticity with minimized resistance to bending. The elongated catheter body may be constructed using a rigid or semi-rigid material, such as, for example, polyether amide (PEBA) or polydimethylsiloxane (PDMS). The outer diameter of the catheter is desirably made as small as possible. Typically, the outer diameter is less than about 3 mm. Preferably, the outer diameter of the catheter body is less than 2 mm.

The guide disks are formed of a material that may be rigid or semi-rigid, but is desirably stiffer (more resistant to bending) than the material of the outer sheath of the catheter or the tubular inner lumen. A notable material for the guide disks comprises poly(ethyleneglycol)diacrylate crosslinked with 2,2-dimethoxy-2-phenylacetophenone.

Figure 2A:
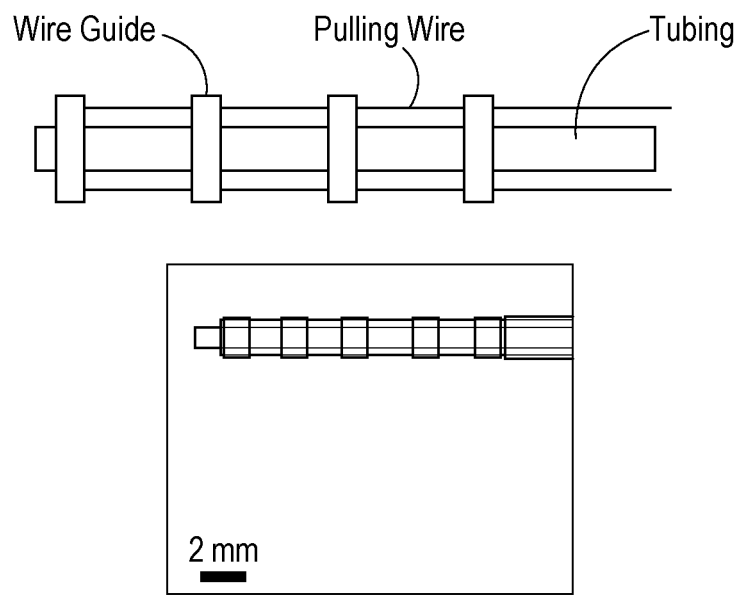
FIGS. 2A-2D show a schematic and photographic views of a steerable catheter device.
Figure 2B:
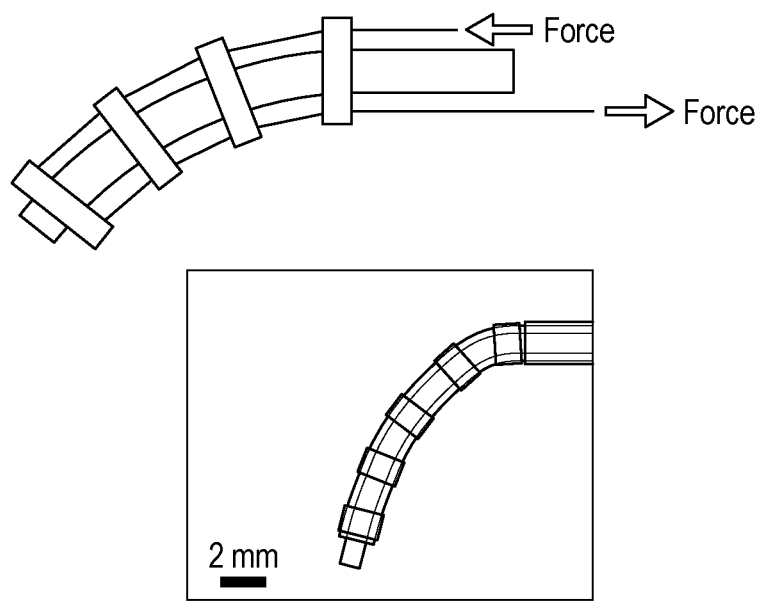
Figure 2C:
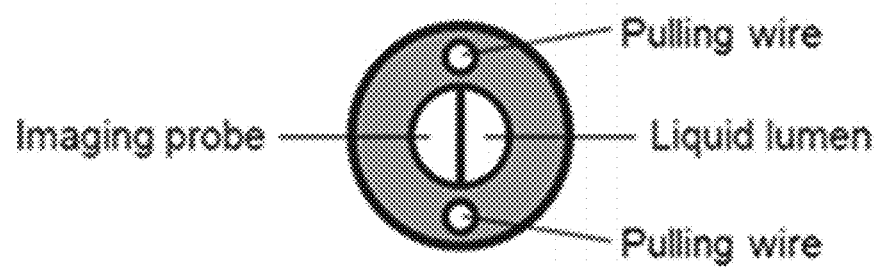
Figure 2D:
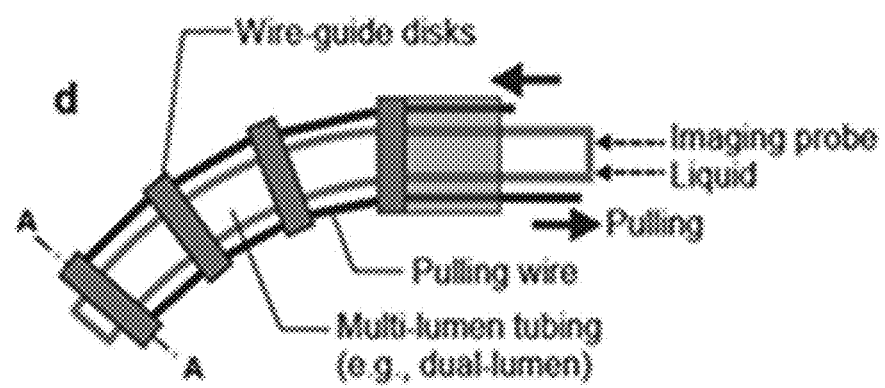

The inner lumen may be used to deploy various instruments, devices such as an imaging device or a sensor, or fluids such as liquids or gases into the desired part of the airway, vessel, lumen, pleural cavity or other bodily cavity. Notably, the desired part may be a subsegmental section of the pulmonary airway. The inner lumen may further be divided into a plurality of lumens to provide a multi-lumen, such as a first lumen and a second lumen, through which an imaging device, an instrument, a device, or a fluid may be placed. The inner lumen(s) can be used to deliver any number of things to assist with opening the cavity, circulation, aspiration, respiration, the decomposition of an obstruction, or the stimulation of healing in the affected area, including air, aspirates, therapeutic agents including drugs, surfactants, biologics, biogenetic agents, nano-particulates, solutions, stem cell and gene therapies, diagnostic agents and tissue scaffolds. Specifically, the catheter could be used for the deployment of liquid therapeutic agents. Suitable therapeutic agents may include but are not limited to solutions, emulsions, or suspensions of biologic, micro- and nano-particulate materials and/or biogenetic materials, cells, microencapsulated genes, drugs, surfactants and the like. Other devices or sensors may also be accommodated through one or more sections of the inner lumen. As shown in FIG. 2C, the inner lumen comprises a tubular member divided into a first lumen for delivery of liquid (and air) into the lung, and a second lumen to accommodate an imaging probe.

The inner lumen is desirably as large as possible to easily pass an imaging fiber or an imaging device (as well as an illumination device) while still capable of allowing the entire catheter to reach into a sub segmental bronchus, such as having an overall outer diameter of about or less than 1.2 mm. In multi-lumen embodiments, the divisions of the inner lumen may be equal or different in size, adapted to allow passage of different devices. Although not shown, other lumens can be included along the length of the catheter as auxiliary-working channels to deliver drugs, agents and/or other micro-instruments and/or assist the bending motion of the distal tip.

In certain embodiments, the inner lumen may comprise a single tubular main inner lumen and a plurality of sub-lumens within the main inner lumen, each sub-lumen having a different purpose. In these embodiments, the need to have partitions in the inner lumen may be reduced or eliminated, thereby simplifying construction of the catheter. For example, a combination of sub-lumens comprising a fluid-carrying sub-lumen for passage of liquid and air, an imaging sub-lumen containing an imaging probe and optionally an additional sensor sub-lumen may be contained within the main inner lumen. Further in some of these embodiments, one or more of the sub-lumens may be movably positioned in the inner lumen, so it can be extended distally from the inner lumen of the proximate section into the distal section or retracted proximally from the distal section into the proximate section.

In some of these embodiments, the tubular main inner lumen may terminate at the distal end of the proximate section of the catheter, and the various sub-lumens extend beyond the proximate section into the space defined by the inner diameter of the guide members in the distal section of the catheter.

In some cases, catheters are used independent of direct visualization. In these cases, catheters are usually placed in the body using indirect visualization such as radiography, sonography or fluoroscopy. In certain advantageous embodiments, the plurality of guide members spaced along the length of the catheter body may comprise radio-opaque materials and may function as imaging markers, in addition to their function as guides for the pulling wires. Such markers can be selected and appropriately positioned in order to reflect the relevant waves of various imaging modalities (e.g., x-ray) in order to allow the use of such modalities to assist with the precise positioning of the catheter. For example, the guide members may include micro- or nano-particles of radio-opaque materials dispersed in a polymer matrix.

Figure 3A:
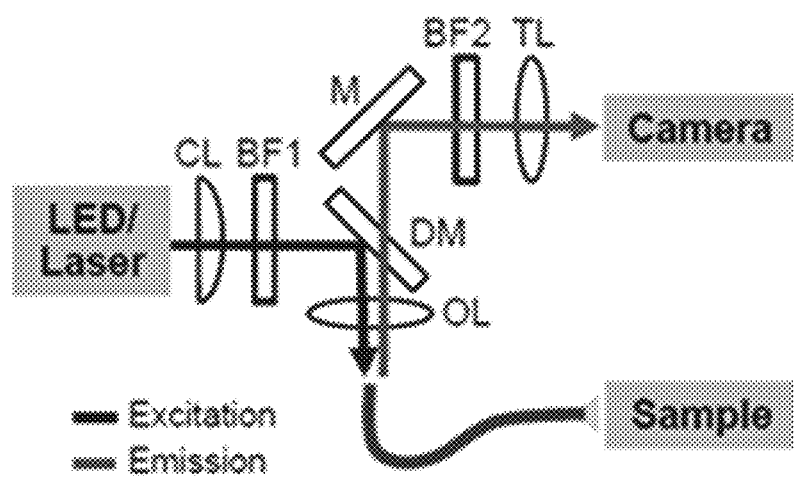
FIGS. 3A-3B show a schematic and photographic views of an imaging system.
Figure 3B:
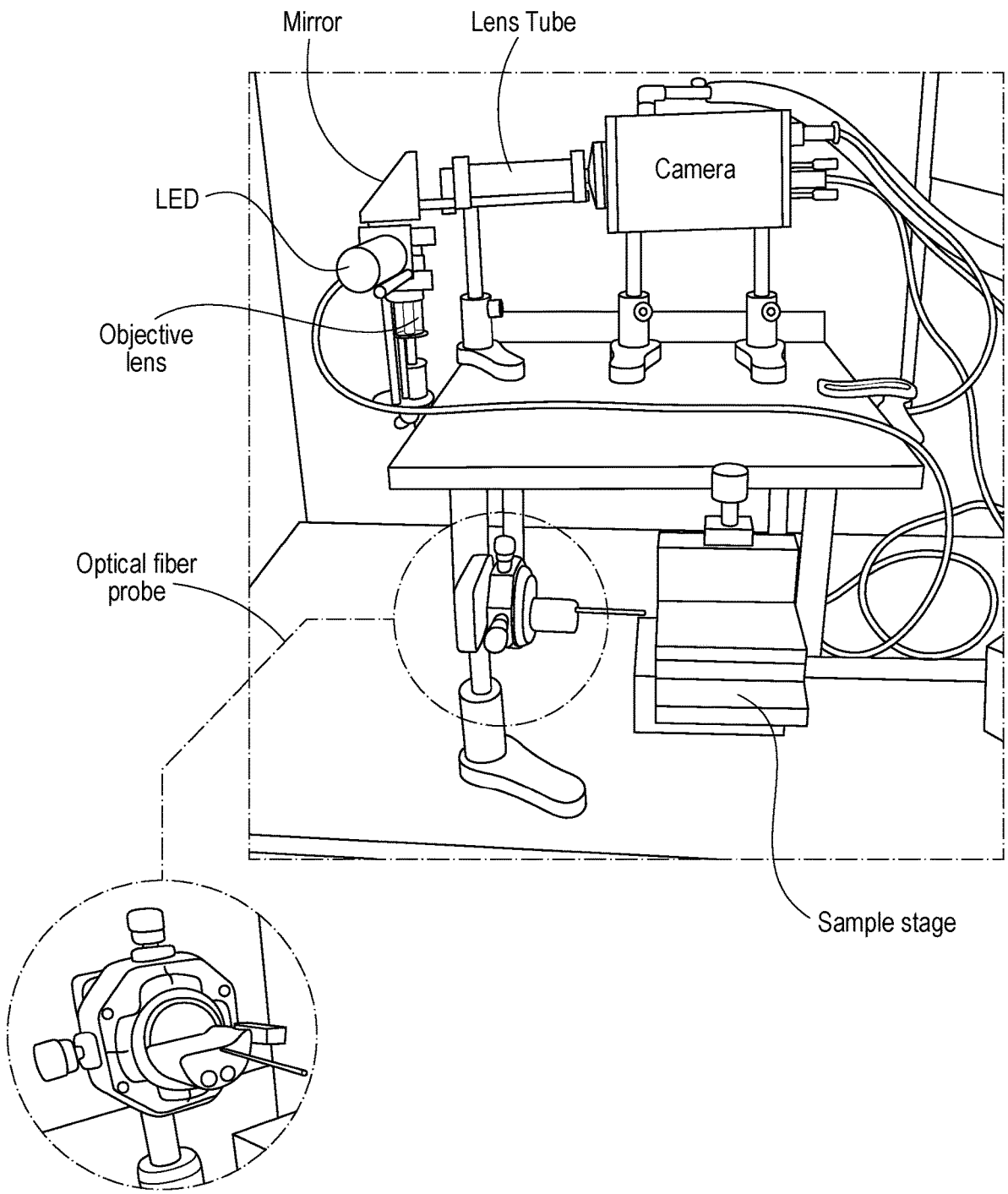

It is desirable that an imaging device is used to help steer the catheter, such as an image fiber or image sensor within the inner lumen of the catheter. FIGS. 3A-3B show a schematic and photographic views of exemplary imaging systems. FIG. 3A shows a schematic of the components of the imaging system, in which excitation radiation including for example, infrared, visible, and/or ultraviolet radiation from a light-emitting diode (LED) or laser source is passed through a series of optical devices into a light pipe directed to a sample (which could include the interior of a lung). Emission from the sample, including fluorescence, heat, UV or visible imagery is returned through a second light pipe through another series of optical devices to a camera for observing and/or recording the images. FIG. 3B shows a photographic view of an imaging setup, including an optical fiber probe, also shown in an inset from another angle, objective lens, LED Mirror, lens tube and camera. A sample stage adapted to hold a rat during an imaging/instillation procedure is also shown. Not shown is a viewing device such as a television screen or monitor, optionally connected to a computer to facilitate viewing, processing and storage of the images. Preferably the imaging system employs optical fiber of about 200 to 300 µm in diameter to enable it to be contained within the constrained dimensions of the inner lumen of the steerable catheter. Optionally the imaging system is movably positioned in the inner lumen, so it can be extended distally or retracted proximally. It may be desirable that the imaging system can be removed completely from the inner lumen to allow passage of other sensor, devices or materials through the inner lumen, once the catheter is positioned.

Figure 4A:
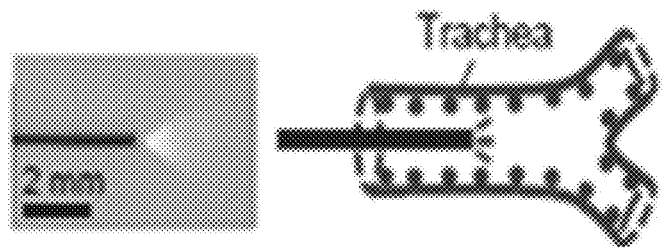
FIGS. 4A-4D show a schematic and photographic views of optical probes and bright-field and fluorescent images obtained using the probes.
Figure 4B:
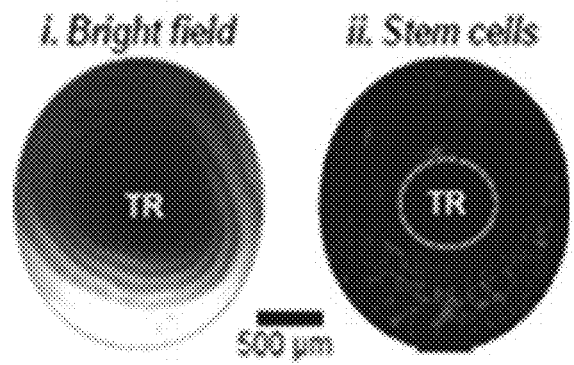
Figure 4C:
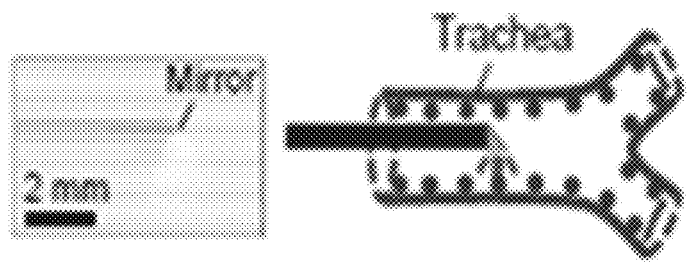
Figure 4D:
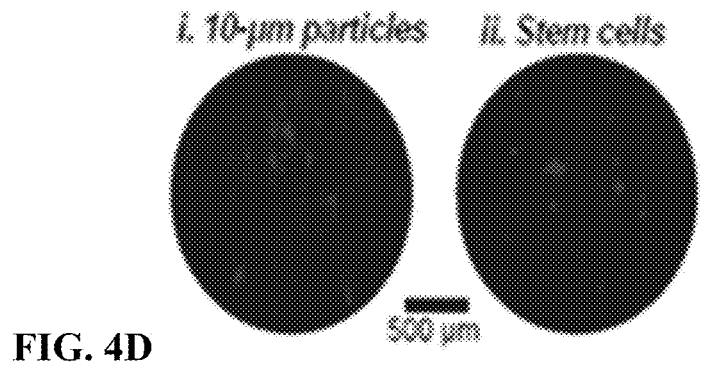

FIG. 4A shows a photograph of the optical probe and a schematic image of the probe within the trachea. Images taken using this optical probe are viewed down the bore of the airway, as shown schematically. FIG. 4B shows the bright-field and fluorescent images of the rat trachea inner surface imaged using the imaging probe after administration of fluorescently labeled therapeutic stem cells to the trachea. FIG. 4C shows a photograph of the optical probe incorporating an optional micro-mirror at the end of the probe and a schematic image of the probe within the trachea. The micro-mirror allows images to be observed at angles away from the longitudinal axis of the probe. For example, a micro-mirror placed at a 45° angle relative to the longitudinal axis provides for viewing images at a 90° angle relative to the longitudinal axis. Images taken using this optical probe with a micro-mirror show the inner wall of the airway, as shown schematically. FIG. 4D shows fluorescent images of the rat trachea inner surface after infusion of fluorescently labeled 10-μm microparticles and therapeutic stem cells.

Figure 5A:
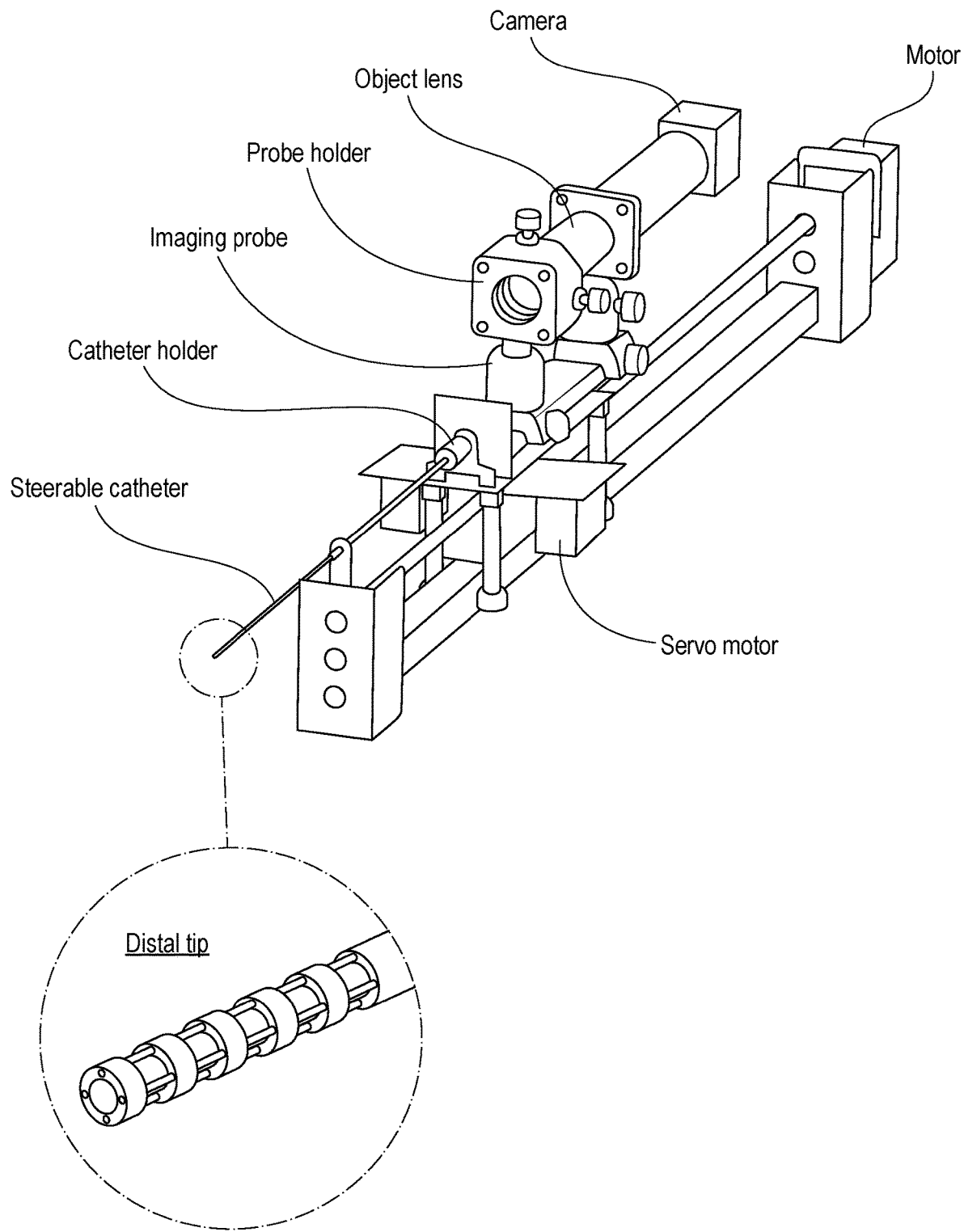
FIGS. 5A-5D show a schematic and photographic views of an image-guided steerable catheter integrated into a navigation control system.
Figure 5B:
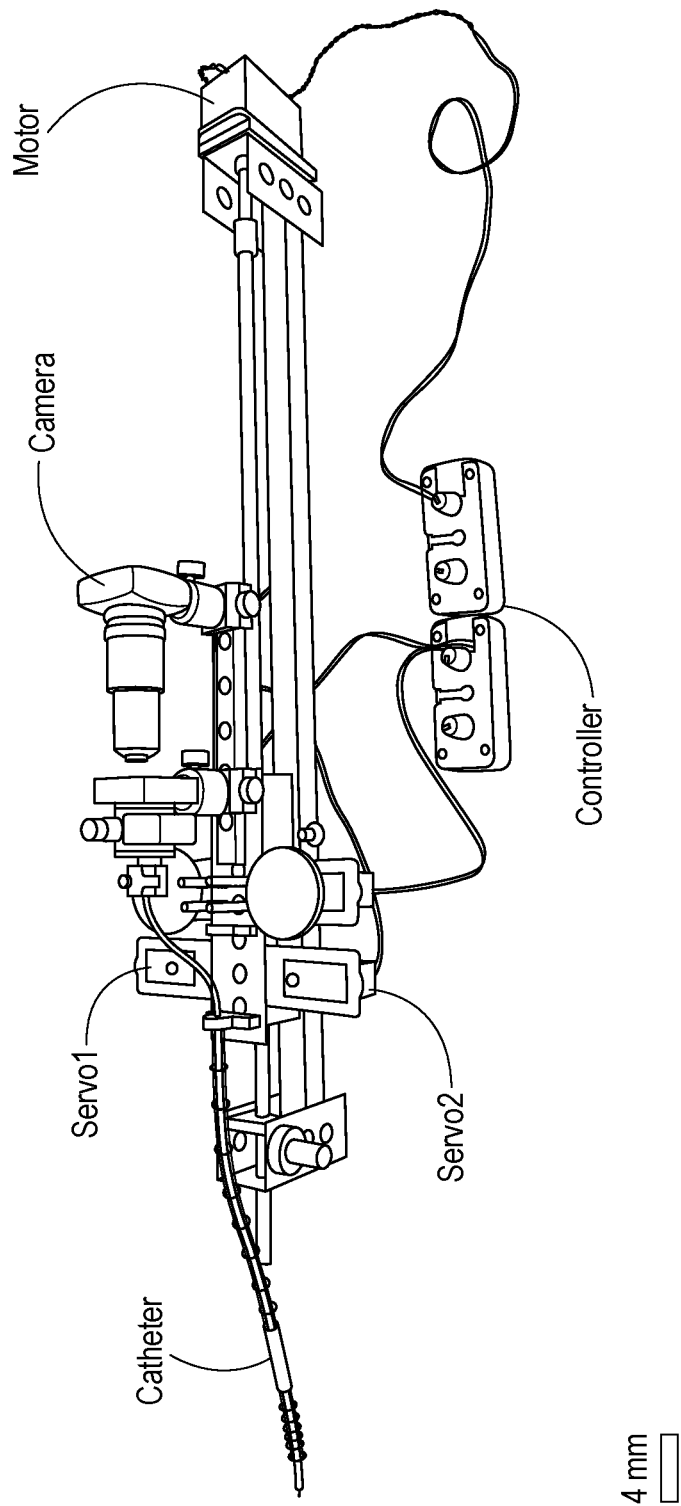
Figure 5C:
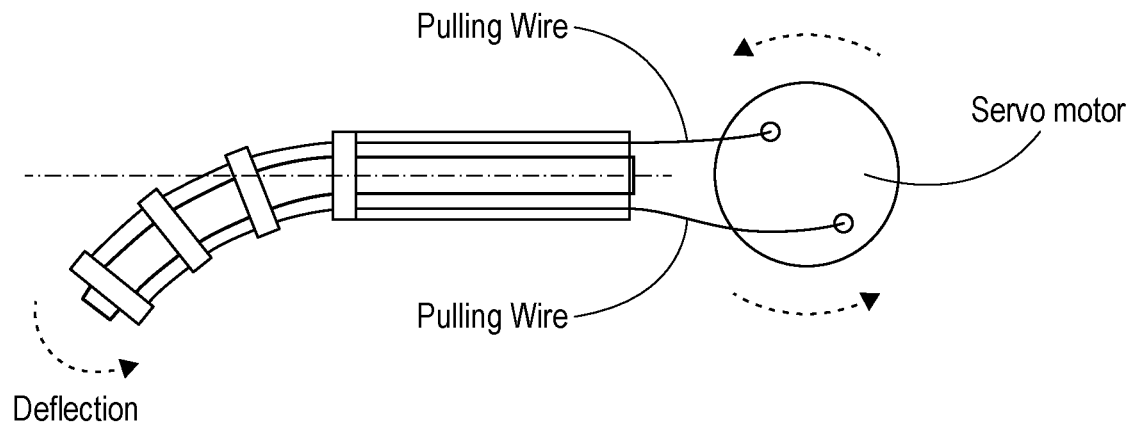
Figure 5D:
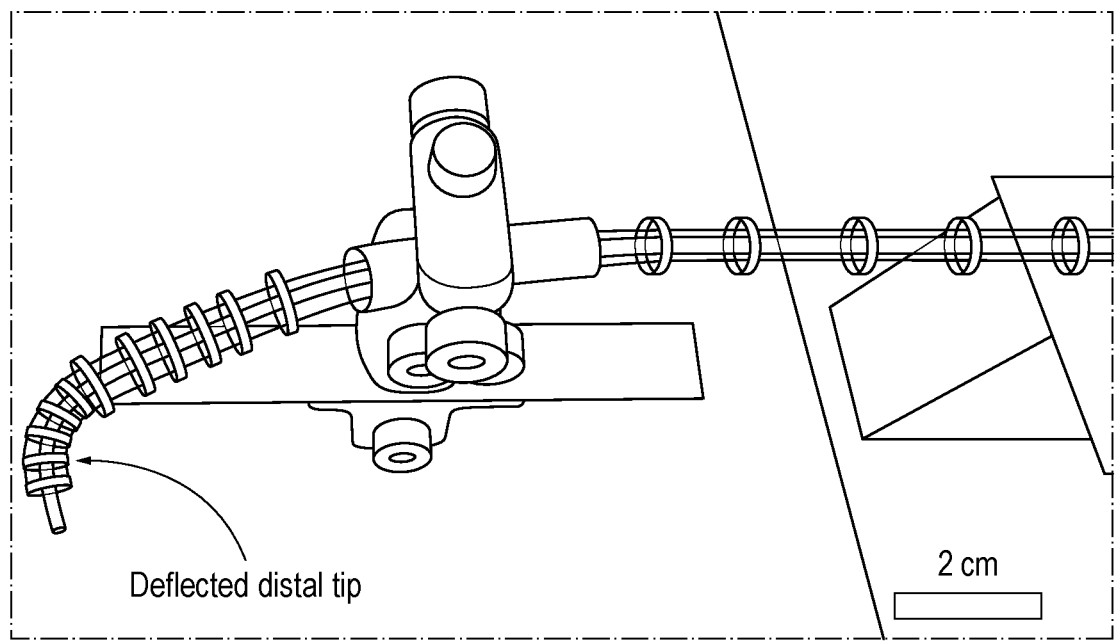

FIGS. 5A-5D show an image-guided steerable catheter integrated into the navigation control system. FIG. 5A is three dimensional CAD drawing of the steerable catheter integrated into the system that control navigation of the catheter in the lung airways. The system illustrated in FIGS. 5A-5D include a microscopic camera that record videos of light signals collected via the imaging fiber bundles. Pulling wires are connected to servo motors that pull or release the wires accordingly to maneuver the deflection of the catheter tip. Translational movement of the catheter-camera unit is controlled by a motor. (Inset: magnified view of the distal tip of the catheter). FIG. 5B is a photographic image of the prototype of the control system. FIG. 5C is a schematic showing deflection of the catheter tip via a servo motor. FIG. 5D is a photographic image of the prototype of the image-guided steerable catheter whose distal tip is deflected via a servo motor.

Deflection of the catheter tip may be accomplished via a servo motor-based controller which selectively and independently controls the tension on the pulling wires. The controller is disposed at the proximate end of the elongate tubular member and operatively engaged to the steering mechanism, wherein the controller is adapted to selectively increase tension force independently to each of the pulling wires of the steering mechanism. The controller is also adapted to selectively reduce tension force or apply extension force independently to each of the pulling wires. A proper combination of increased tension force to at least one pulling wire while reducing tension force or applying extension force to a second pulling wire will cause the distal section of the catheter to bend in the direction of the first pulling wire. For example variation of force to the pulling wires may be done mechanically with a combination of pulleys, wheels, levers, gears, cams, servo motors, etc. The controller also may advance or retract the device, such as through the airway, using additional servos. The controller may be in connection to a hand held device such as a joystick that includes a control mechanism or a plurality of control mechanisms that can be articulated to any location along a 360° circle and translated in any plane. In doing so, the distal tip will bend accordingly in three-dimensional space. Alternatively the controller may control the force applied to the pulling wires in response to electric signals from an electronic control device such as a graphical user interface, mouse, touchpad, touchscreen, or the like, operated in conjunction with a computer. In some embodiments, steering of the distal tip is controlled autonomously by a computer, preferably using machine-vision target identification.

As illustrated schematically in FIG. 5C, in some embodiments two diametrically opposed pulling wires are operationally connected to a single servo comprising a wheel and a motor, wherein the servo motor provides rotational motion to the servo wheel, and the diametrically opposed pulling wires are connected to the servo wheel so that rotational motion of the servo wheel provides tension force to a first of the two pulling wires and extension force to the second of the two pulling wires, thereby deflecting the distal tip toward the wire under tension as shown in FIG. 5D.

Figure 6:
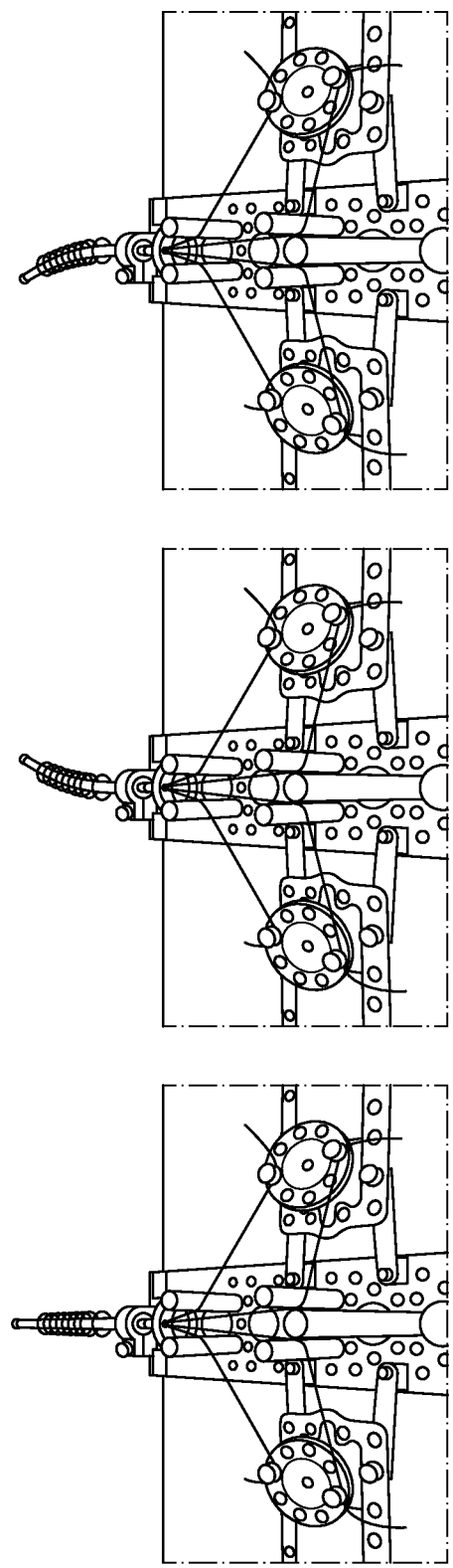
FIG. 6 shows continuous detection and tracking of a target.

As shown in FIG. 6, in some embodiments comprising four pulling wires, the pulling wires comprise two pairs of diametrically opposed pulling wires and each pair is operationally connected to a single servo comprising a wheel and a motor, wherein the servo motor provides rotational motion to the servo wheel, and the diametrically opposed pulling wires are connected to the servo wheel so that rotational motion of the servo wheel provides tension force to a first of the two pulling wires and extension force to the second of the two pulling wires, thereby deflecting the distal tip toward the wire under tension. In these embodiments, one pair of pulling wires controls "up-down" motion of the distal tip relative to the robot arm, and the other pair of pulling wires controls "left-right" motion of the distal tip relative to the robot arm to steer the device toward a target.

Figure 7:
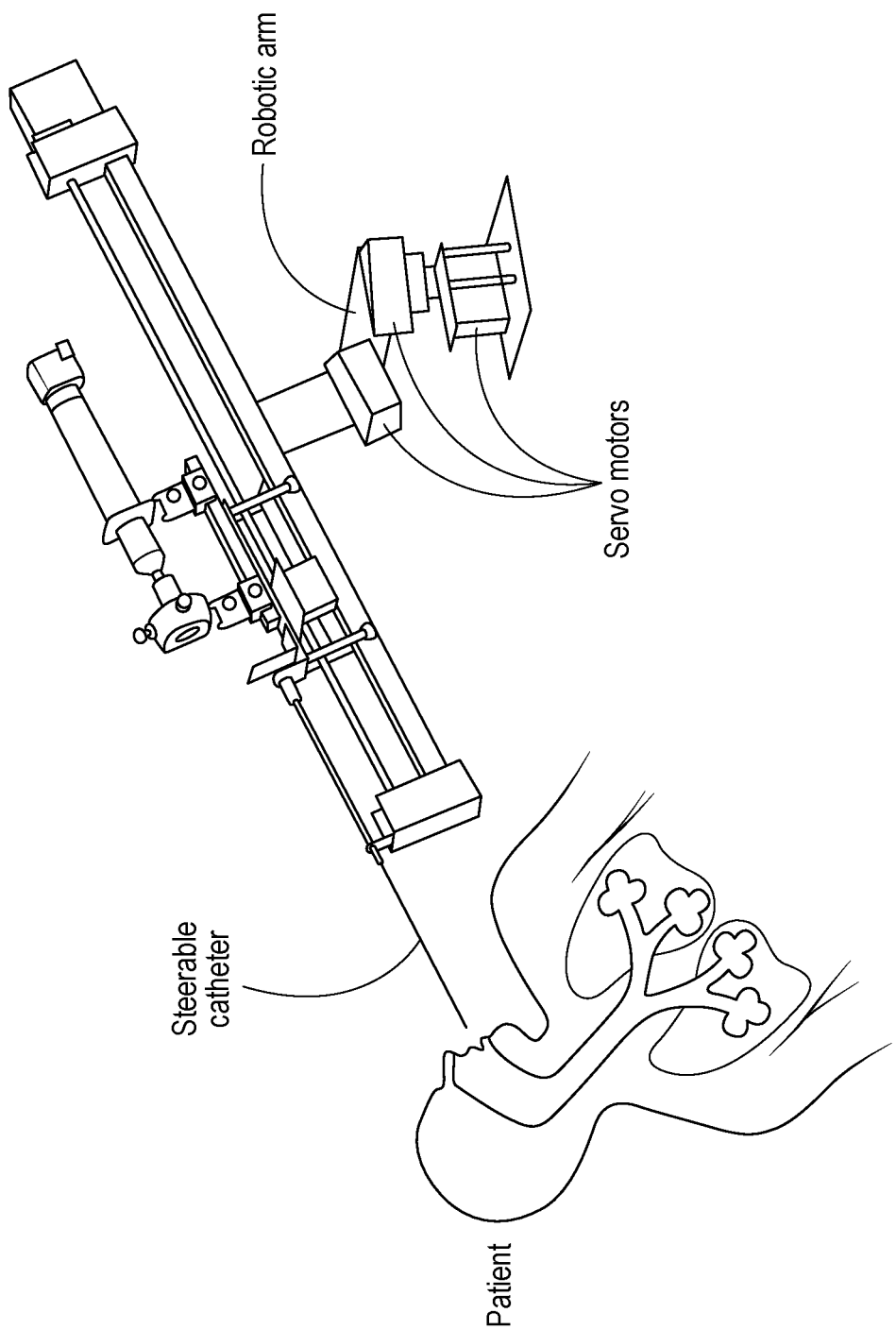
FIG. 7 shows a schematic of a steerable catheter-navigation system supported on a robotic arm.
Figure 8:
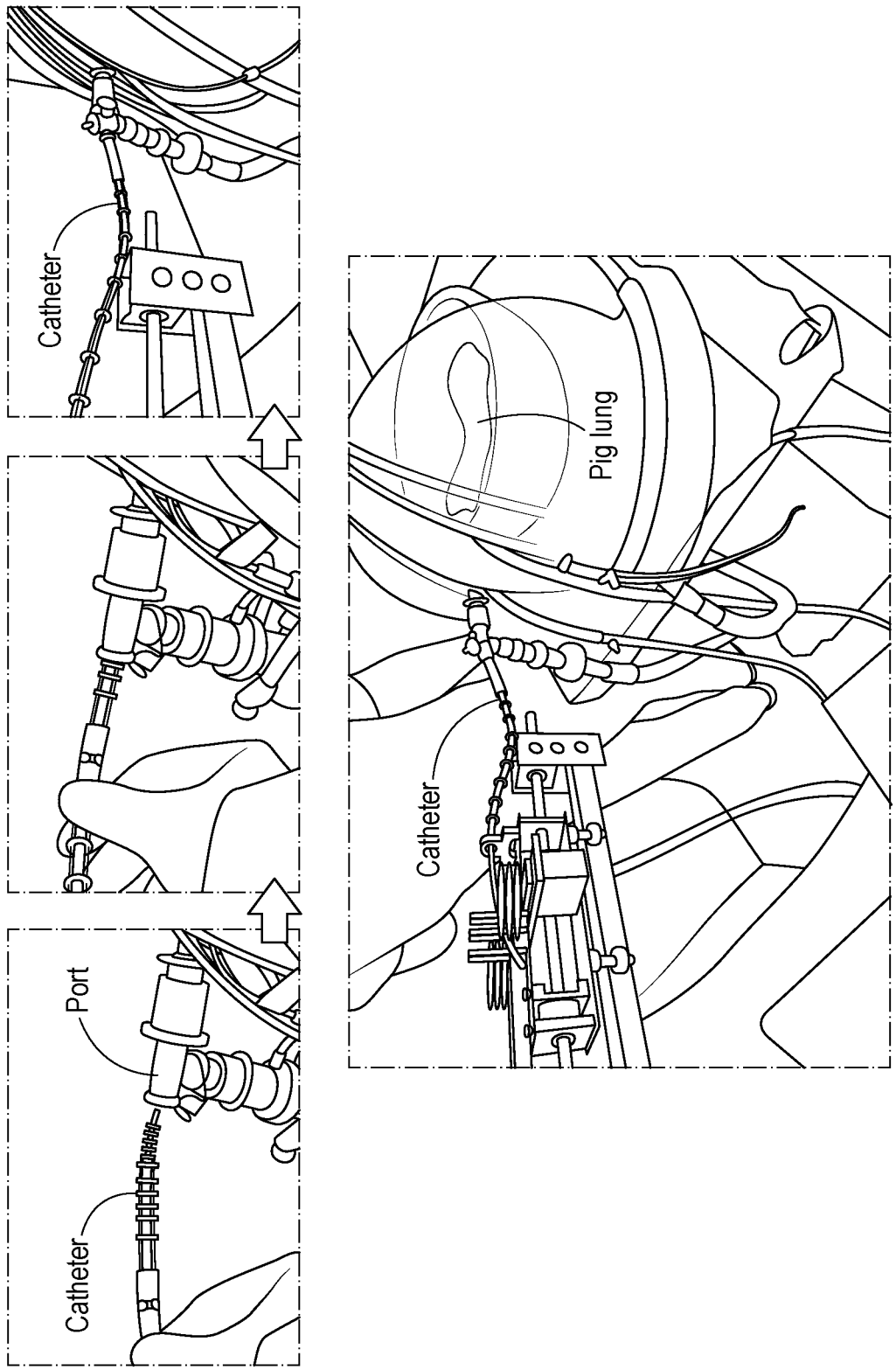
FIG. 8 shows testing of the steerable catheter device prototype using explanted pig lungs.

As shown in FIG. 7, the steerable catheter-navigation system may be supported on a robotic arm. The catheter-navigation control system can be mounted onto a computer-controlled robotic arm whose movements are maneuvered via servo motors. This configuration increases structural flexibility of the system adding more freedom of movement to the system and thus facilitates oral or nasal insertion of the steerable catheter into the patient's lung. FIG. 8 shows testing of the steerable catheter device prototype using explanted pig lungs.

In addition to drug delivery, this automated robotic device can be used for additional clinical applications as follows: Collection of tissue samples at selected airway regions using biopsy tools introduced via the robotic device; Collection of lung fluid samples at selected airway regions by aspiration of the fluid through a lumen of the robotic device; Optically based disease diagnosis at local airways via an optical fiber integrated into the robotic device.

Figure 9:
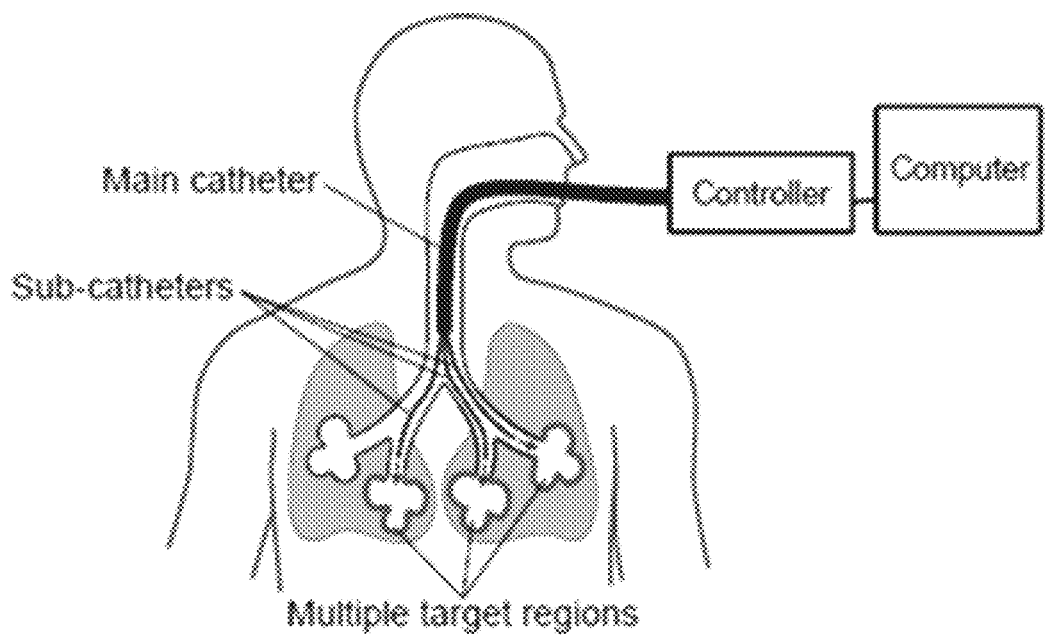
FIG. 9 shows a schematic view of drug administration to multiple target lung regions using multiple autonomously driven drug delivery catheters.

FIG. 9 shows drug delivery to multiple lung regions using an autonomous catheter. Multiple sub-catheters are deployed from a main catheter where each catheter is autonomously driven via machine vision technology to its own target region in the patient's lung. This allows rapid, simultaneous drug delivery into multiple target lung regions with minimal human intervention and great spatial precision.

Methods for preparing micrometer-scale profiles using three dimensional (3D) printing techniques are useful for preparing the guide members of the steerable catheter. Embodiments of the method comprise: placing a composition comprising a photocrosslinkable water-soluble polymer and a photocrosslinking agent between spaced apart transparent sheets; shining light in a desired pattern through the composition, thereby crosslinking a portion of the composition to provide a crosslinked profile in the desired pattern; and removing the non-crosslinked portion of the composition from the crosslinked portion.

Notable photocrosslinkable water-soluble polymers include poly(ethylene glycol) diacrylate or poly(ethylene glycol) dimethacrylate. These polymers are available commercially in a variety of molecular weights and are water-soluble or miscible. They can be crosslinked using 2,2-dimethoxy-2-phenylacetophenone (DMAP) irradiated at around 405 nm.

Figure 10A:
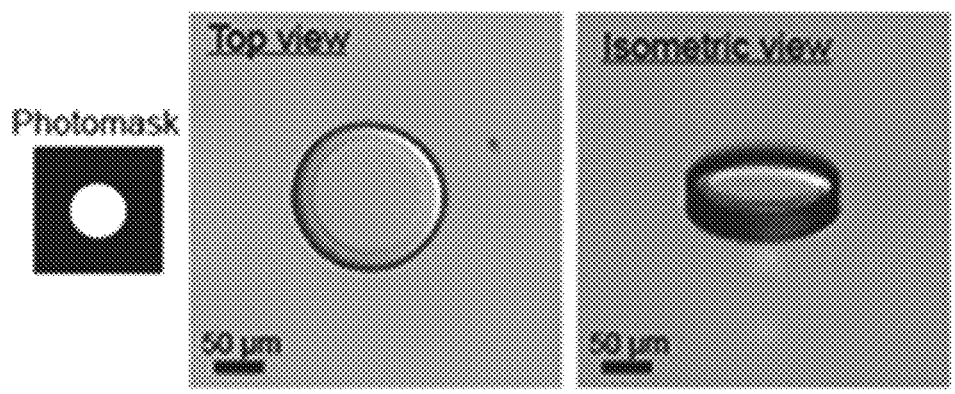
FIGS. 10A-10D show aspects of a three dimensional printing system useful for preparing guide members of a steerable catheter.
Figure 10B:
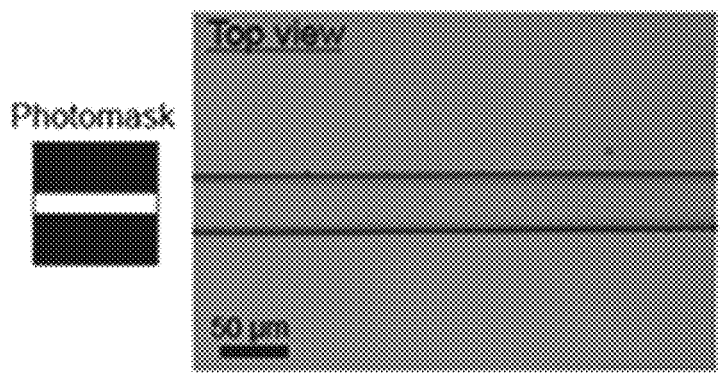
Figure 10C:
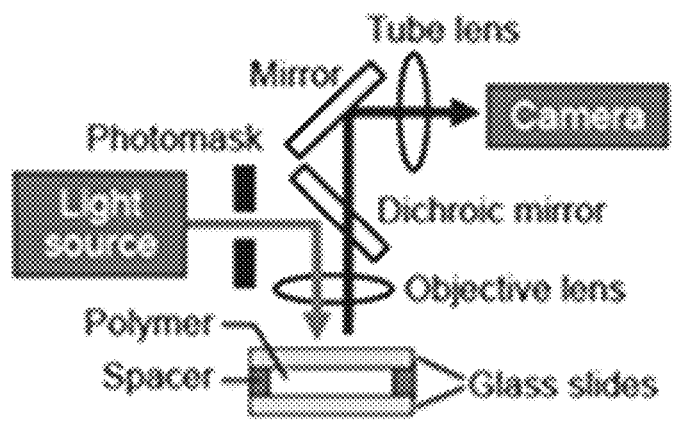

As shown in FIGS. 10A-10D, the desired pattern can be obtained by placing a photomask or digital micro-mirror between the light source and the crosslinkable composition. FIG. 10A shows photographic top view and isometric view of a disk prepared using a circular photomask. The disk is about 25 μm thick and about 200 μm in diameter. FIG. 10B shows a bar with a rectangular cross-section (about 25 μm×50 μm) prepared using a slit photomask. A schematic of the three dimensional printing system using a photomask is shown in FIG. 10C. In these examples, the space between the glass slides is about 25 μm. The photomask blocks light transmission from the light source to the uncrosslinked composition in a pattern defined by the shape of the photomask. In these examples, the light source was a 405 nm LED powered at 410 mW. Light that passes through the photomask initiates crosslinking when it impinges on the composition. The uncrosslinked portion of the composition can be removed from the crosslinked portion of the composition after photo-crosslinking by dissolving it in water. The procedure used for these examples comprises: (i) filling the space between the glass slides separated by the spacer with a mixture comprising poly(ethylene glycol) diacrylate and DMAP; (ii) placing a photomask in front of the light source to illuminate a light pattern with a desired shape into the mixture; (iii) exposing the composition to the light pattern for about 5 to about 20 seconds (such as about 10 seconds) to crosslink the portion of the composition illuminated by the light pattern; and (iv) removing the uncrosslinked portion of the composition by dissolving it in water.

Figure 10D:
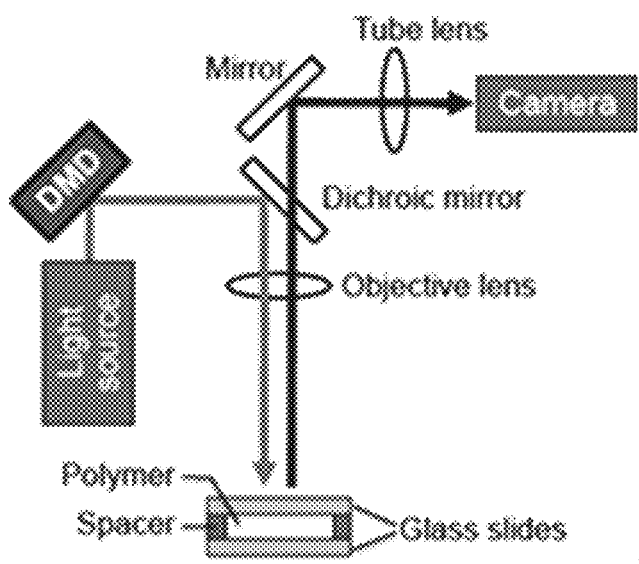

FIG. 10D shows a schematic of an alternative three dimensional printing setup using a digital micromirror device (DMD). The digital micromirror device is an optical semiconductor. A DMD chip has on its surface several hundred thousand microscopic mirrors arranged in a rectangular array that correspond to the pixels in the image to be transmitted. The mirrors can be individually rotated ±10-2°, to an on or off state. In the on state, light from the projector bulb is reflected into the lens making the pixel appear bright on the screen. In the off state, the light is directed elsewhere (usually onto a heat sink), making the pixel appear dark. The DMD can provide fabrication of the guide members with increased spatial resolution and pattern generation speed than using photomask techniques.

Figure 11A:
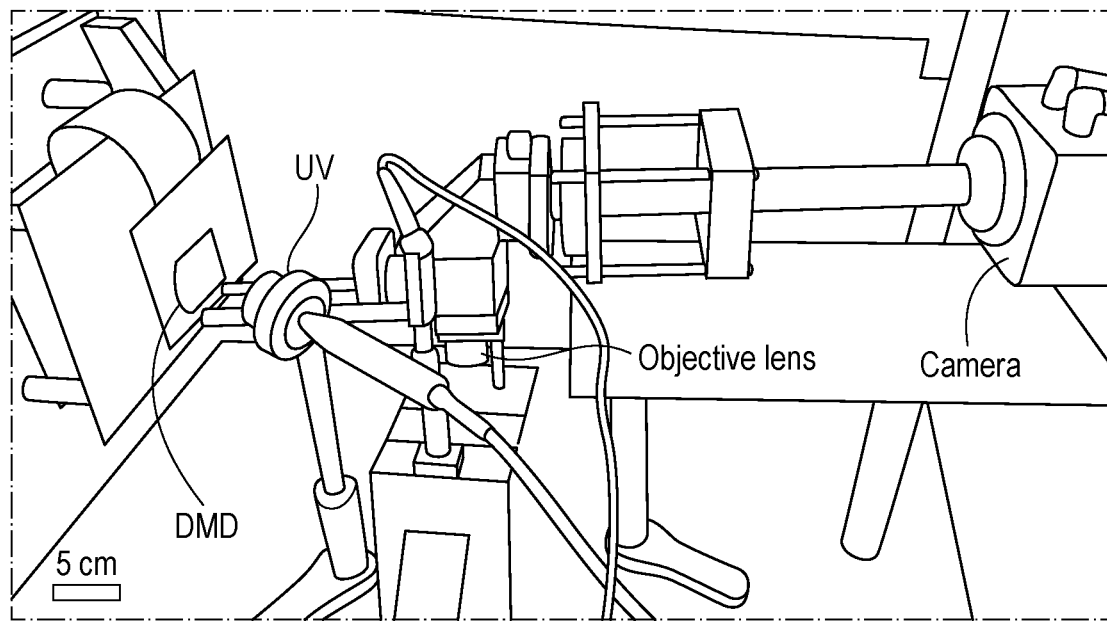
FIGS. 11A-11C show schematic and photographic view of three dimensional printing of wire-guide disks that generate deflection movement of the catheter distal tip.
Figure 11B:
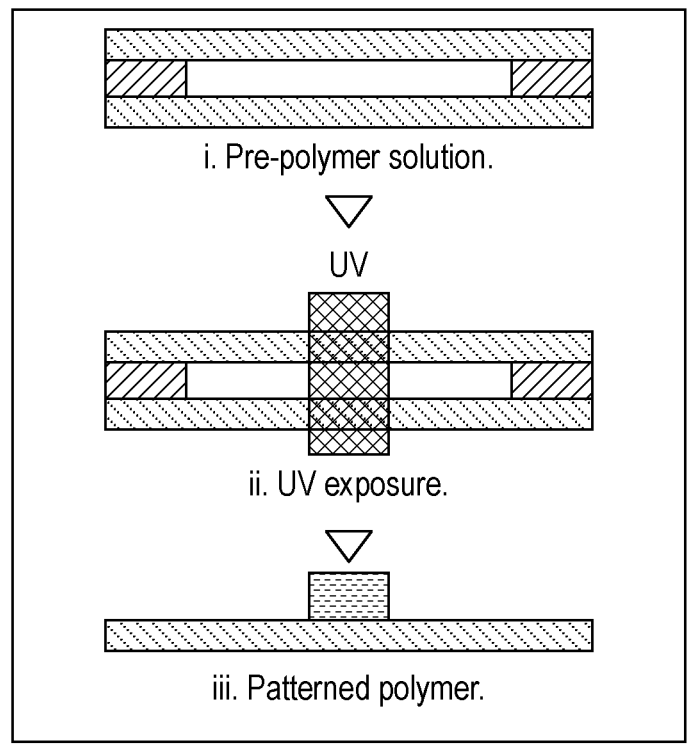
Figure 11C:
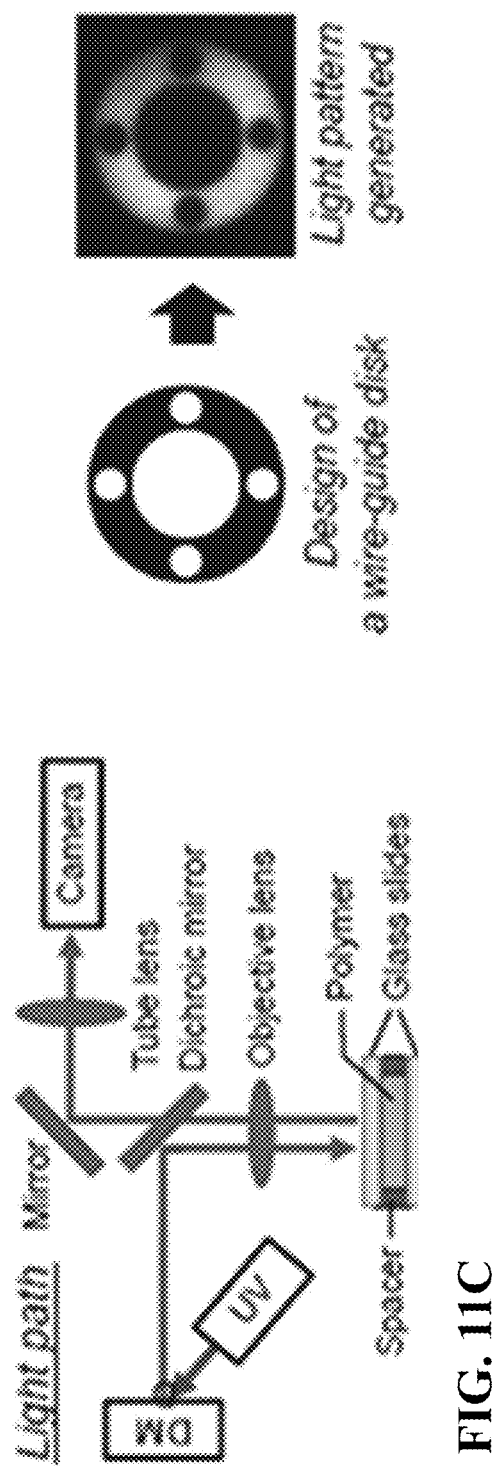

FIGS. 11A-11C show an alternative three-dimensional printing of wire-guide disks that generate deflection movement of the catheter distal tip. FIG. 11A is a photographic image of a custom-built three-dimensional printing system that allows for rapid production of guide-wire disks. FIG. 11B is a schematic showing the three-dimensional pattering process of the disks. FIG. 11B shows that the photo-crosslinkable pre-polymer solution is filled in a chamber and excitation light is illuminated to the pre-polymer solution. The un-exposed pre-polymer solution is washed away leaving the patterned polymer. FIG. 11C is a schematic of the light path of the three-dimensional printing system. Excitation light that can cross-link polymer is illuminated onto digital mirror device (DMD) that creates desired disk pattern onto the chamber filled with the pre-polymer solution.

Figure 12A:
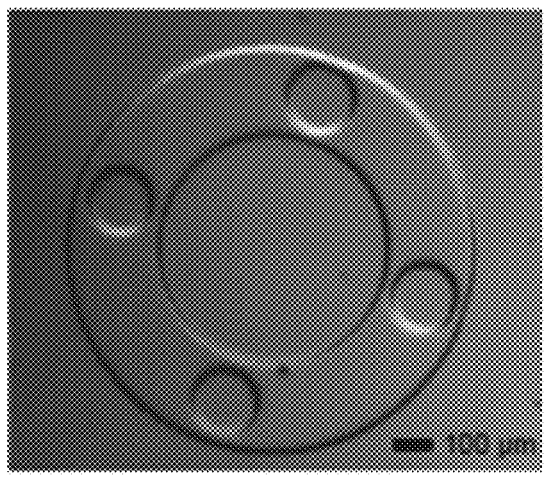
FIGS. 12A-12C show three dimensional printed wire-guide disks.
Figure 12B:
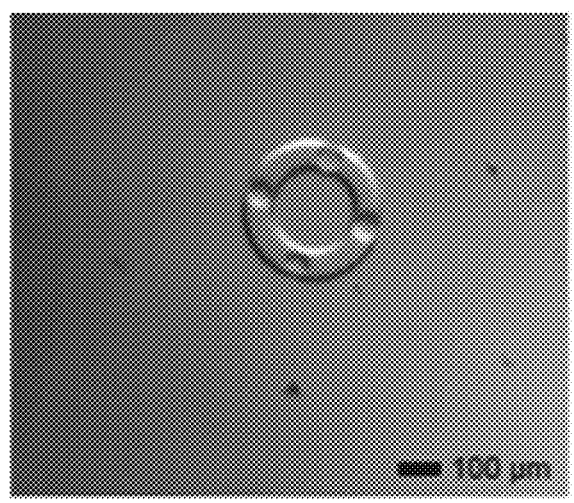
Figure 12C:
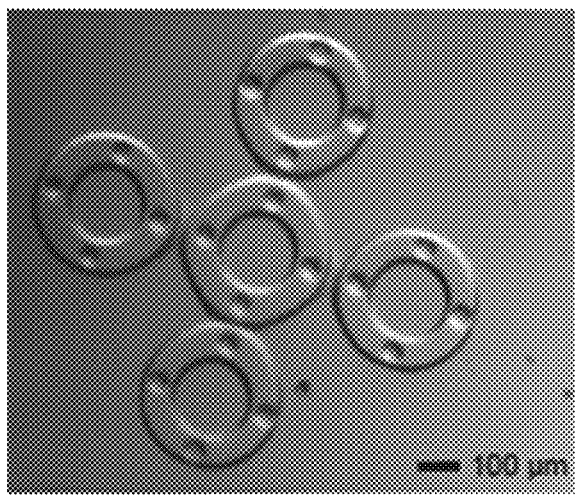

FIGS. 12A-12C show three dimensional printed wire-guide disks. FIG. 12A shows a disk with outer diameter of ~1 mm (b) and ~300 µm were generated using the custom-built three-dimensional printing system. FIG. 12C shows multiple disks (e.g., 5 disks) with outer diameter of ~300 µm were produced rapidly with a single exposure using the system.

Figure 13A:
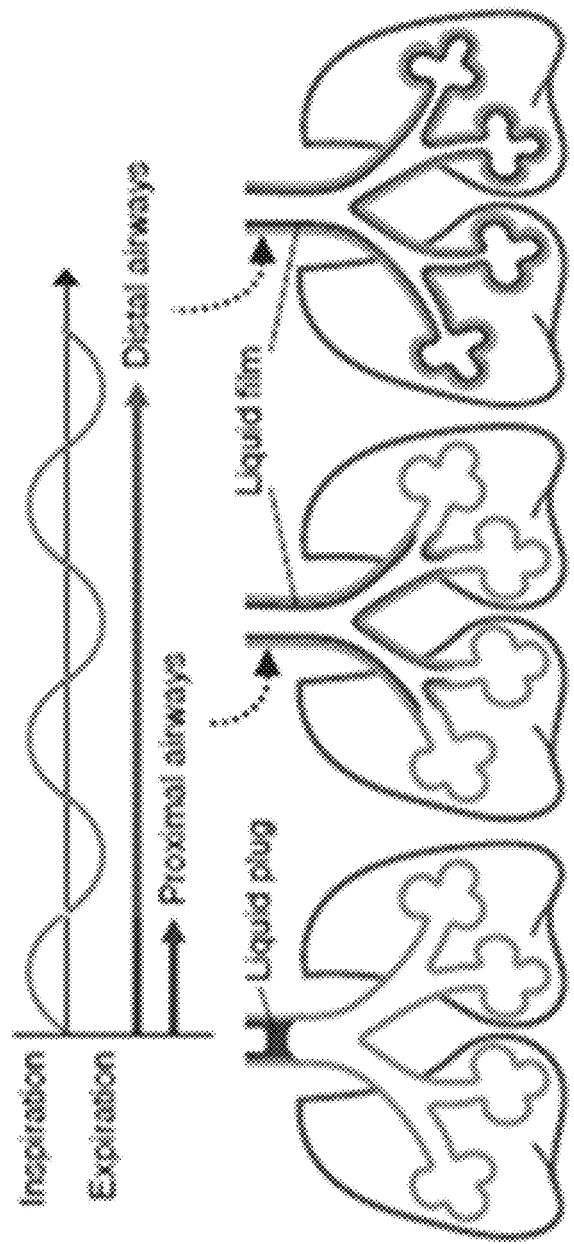
FIGS. 13A-13D show a schematic overview of liquid film deposition by plug instillation.

FIGS. 13A-13D illustrates schematically the method of delivery of a liquid film into a lung after deposition of a liquid microvolume onto the inner surface of the pulmonary airway. The method comprises forming a plug of the liquid across the diameter of the pulmonary airway; and transporting the plug distally through the airway with air pressure delivered from the inner lumen of the catheter depositing a film comprising a portion of the liquid microvolume. The general method is shown in FIG. 13A, in which a liquid plug is introduced into the pulmonary airway, such as in the trachea or proximal airways, and a film of the liquid is transported to distal airways during several inspiration/expiration cycles. Liquid film can be delivered to the proximal airways by instilling a small liquid plug and inspiring air or to the distal airways by repeated cycles of plug transport, rupture, and reformation during continued ventilation.

Figure 13B:
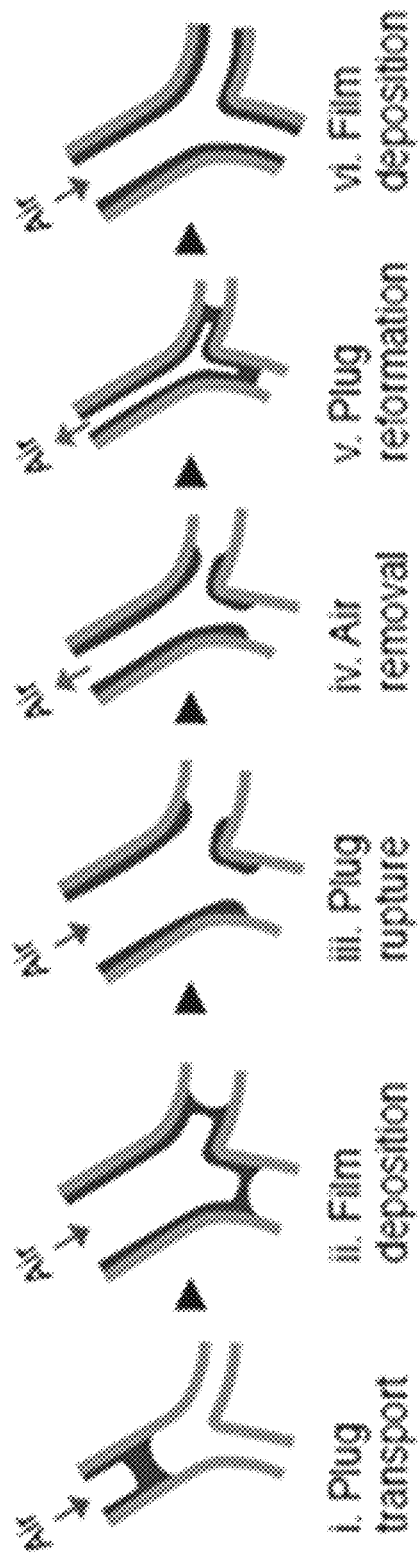
Figures 13C, 13D:
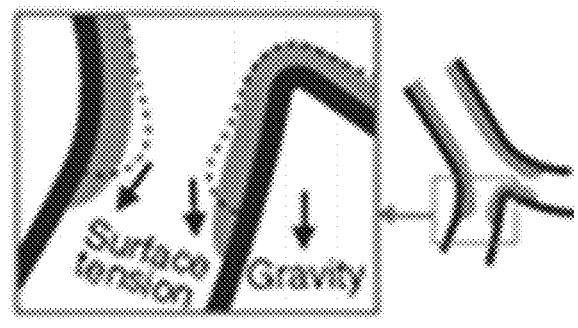

The method is illustrated schematically more specifically in FIG. 13B. Steps of the method include (i) installation of a liquid plug into an airway by positive air pressure and (ii) liquid film deposition on the airway surfaces by moving plugs distally by application of positive air pressure. A liquid plug introduced into an airway (rat trachea or clinically, a bronchus of the human lung via catheter) is moved deeper into the lung by positive air pressure. Movement of liquid film deposited on airway surfaces can also be induced by surface tension gradients and gravity (FIG. 13C). During inspiration, as the plug travels through the airway, it deposits a thin film on the airway surface and splits into smaller plugs at bifurcations in downstream airways, splitting into increasingly smaller plugs at more distal bifurcations while leaving a thin liquid layer along the airway surfaces.

A liquid plug traveling along a tube decreases its volume due to deposition of a liquid film layer and eventually ruptures, producing a liquid collar; as shown in FIG. 13B. The plugs rupture before the end of the first inspiration, resulting in the generation of a liquid film in the target airway, which can be specified by selecting the plug volume and airflow rate. A decrease in airway diameters occurs during expiration (air removal), followed by plug reformation due to sufficient reduction in airway diameter. A liquid film deposited on the inner lung surface reforms into a new liquid plug when its volume exceeds a critical value. Due to the decreasing diameters in recoiling small airways, a liquid layer can thicken, become unstable, and reform into a new plug. In subsequent inspiration/expiration cycles, continued film deposition by transport of reformed plugs is shown in FIG. 13B. To deposit liquid into the deeper lung, liquid plugs are instilled such that they rupture in smaller airways, where airway diameters change significantly during ventilation, allowing plug reformation. With repeated plug transport, rupture, and reformation, film deposits all of the way into the alveoli.

FIG. 13D shows a comparison of airway diameters of humans and rat lung models, including the estimated difference in diameters during inspiration and expiration. The smallest bronchus of the human proximal airway has a diameter of about 2.8 mm during inspiration. This defines an approximate upper limit for the diameter of a catheter adapted to reach into subsegmental portions of the airway. In comparison, the diameters of rat airways are significantly smaller, so investigation of the installation technique can be carried out on rat models with fewer transitions through distal bifurcations than in humans. Inspiration and expiration can be accomplished by moving air through the catheter by use of a ventilator fluidly connected to the proximal end of the inner lumen of the catheter. In some cases, natural or assisted breathing of the patient provides the inspiration/expiration cycles.

Accordingly, the method further comprises forming secondary plugs at branches within the pulmonary airway. The method further comprises rupturing the plug by increasing air pressure delivered from the inner lumen of the catheter and extending the film of the liquid distally in the pulmonary airway. The method further comprises reforming plugs of the liquid by applying reduced air pressure from the inner lumen of the catheter.

The method of delivery of a liquid to a targeted area of the lung comprises a process wherein the liquid is transported to distal regions of the lung by repeated cycles of plug transport, rupture and reformation during continued ventilation; wherein a plug of the liquid is instilled into the airway by inspiration or positive air pressure, a film of the liquid is deposited on the airway surfaces by a moving plug, the plug ruptures on the airway surface due to positive air pressure, the airway diameter is decreased during expiration or negative air pressure, the plug reforms due to sufficient reduction in airway diameter, and continued film deposition by transport of the liquid plugs by positive air pressure.

Liquid film deposition in a targeted region of the lung can be achieved by varying the initial plug volume, liquid viscosity and ventilation parameters. The plug volume and ventilation conditions can be determined by mathematical modeling of plug transport in a tubular geometry, as described in greater detail in Kim, et al., *Applied Physics Letters*, 107, 144101 (2015) and Kim et al. *Proceedings of the National Academy of Sciences*, 112(37), 11530-11535 (2015).

FIGS. 14A-14C show schematic views of an embodiment wherein cells or particulates, such as but not limited to therapeutic agents, entrained in the liquid are deposited onto the inner surface of the airway using the steerable catheter described herein. FIG. 14A shows a schematic of the steerable catheter inserted into the airway through the trachea and a liquid plug instilled in a bronchus. FIG. 14A shows cells and particulates dispersed randomly through a liquid matrix within the liquid plug instilled in the airway by intratracheal infusion. As the plug travels down the airway and ruptures as previously described, it deposits a thin film of liquid and the cells and/or particles onto the airway surface. FIG. 14B shows a schematic view of the typical flow velocity profile of a liquid plug traveling down an airway. It also shows that the shape of the liquid plug comprises leading and trailing menisci whose shapes are determined by among other things, surface tension of the liquid, contact angle and other variables known in the art of fluid mechanics. The motion of the plug in the direction of the arrow creates circulating currents within the liquid plug as indicated by the small dashed arrows. These currents keep the cells and/or particles suspended in the liquid plug as it travels down the airway. FIG. 14C shows a force diagram of particles or cells suspended in the liquid plug. $F_V$ is the force propelling the liquid plug down the airway. $F_B$ is a force of the eddy current within the liquid plug directed toward the center of the plug and $F_G$ is a force of the eddy current within the liquid plug directed toward the outside of the plug near the inner surface of the airway. As the liquid plug travels down the airway it leaves a trailing film whose thickness h decreases as the plug moves farther away. Particles are driven by $F_G$ toward the airway surface and into contact with it. Particles randomly distributed within the liquid plug will as a result be randomly distributed onto the surface of the airway. More detailed discussion on the particle and cell seeding via small liquid plugs is given in Kim et al., *Scientific Reports*, 7:13082, (2017).

Figure 15A:
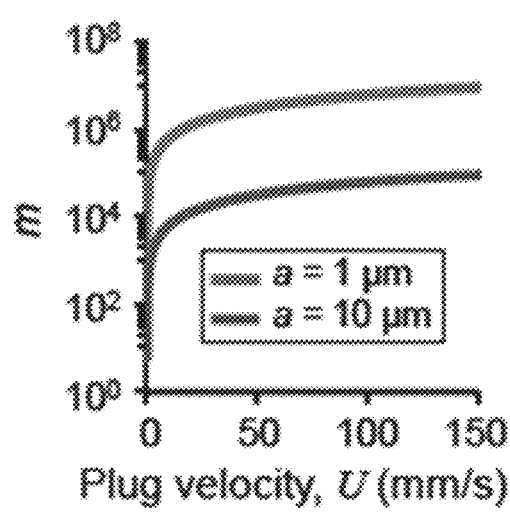
FIGS. 15A-15D show charts of the parameters involved in deposition of particles onto a tubular surface by liquid plug instillation.
Figure 15B:
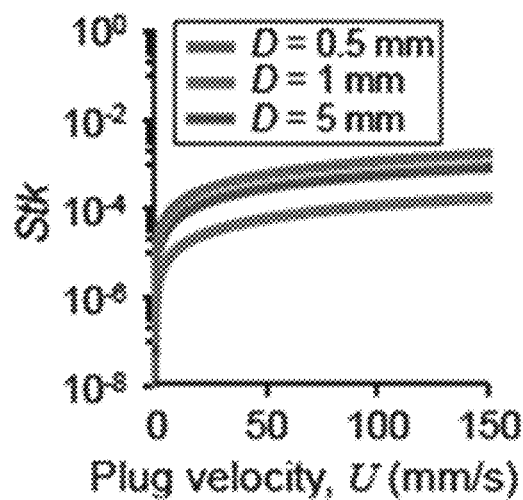
Figure 15C:
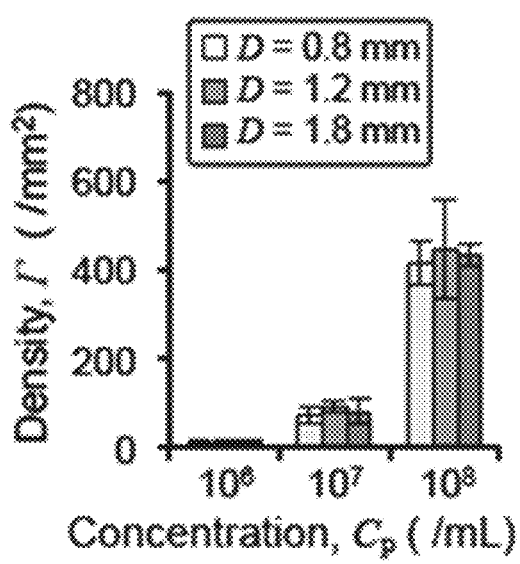
Figure 15D:
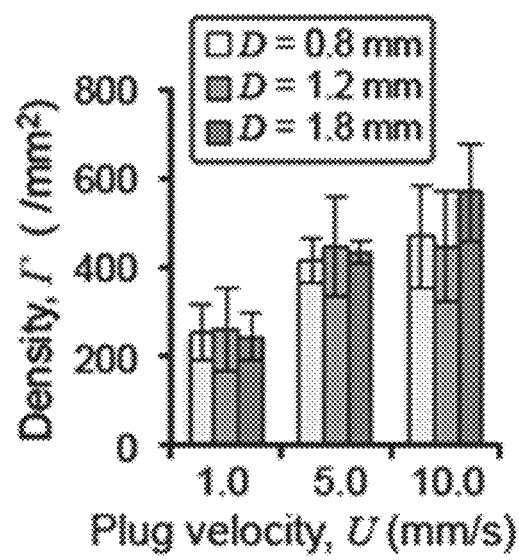

The mechanics of microparticle transport and deposition in a tubular channel can be quantified according to variables summarized in FIGS. 15A-15D. As shown in FIG. 15A, the movements of microparticles with diameters of 1 μm or 10 μm are mostly affected by viscous force induced by the liquid flow onto the particles as the ratio of viscous force to gravity force "m" are much greater than 1. Microparticles can readily flow with the liquid as their Stokes numbers "Stk" are much smaller than 1 for various tube diameter "D" as shown in FIG. 15B. Surface coverage density of microparticles "F" increases with the concentration of particles "CP" mixed in the liquid plug instilled (FIG. 15C) and velocity of the plug "U" introduced into the channel (FIG. 15D).

The experimental and modeling data suggest that instillation of microvolumes of liquid into a ventilated pulmonary airway could be an effective strategy to deliver exact doses of drugs or other therapeutic or diagnostic agents to targeted pathologic regions of the lung, especially those inaccessible by bronchoscopy, to increase in situ efficacy of the drug and minimize systemic side effects. The method can be used to introduce both liquid and solid agents that can be suspended in a carrier liquid.

Clinical pulmonary drug delivery could be facilitated by the procedures for plug instillation into the lung described herein using the steerable catheter described. Alternatively, a multilumen balloon catheter could be inserted near a target region and used to deposit drug onto the isolated airway surfaces, while the patient is supported by gas exchange in other parts of the lung. Drugs contained in the liquid film could more effectively diffuse and absorb into the epithelium, improving therapeutic effects. Optimal outcomes could result from the clearance of mucus before plug instillation (e.g., by the delivery of mucolytics or lung lavage).

The clinical utility of this liquid delivery approach could extend to treating lung cancer and a range of acute and chronic pulmonary diseases. For example, high concentrations of mucoactive agents instilled with liquid plugs could help dissolve the mucus layer formed in the airways by many lung diseases, reducing complications and providing long-term benefits. For single cancer lesions, microvolume plugs containing high concentrations of chemotherapeutics can be delivered directly to the site of the tumor as a (neo)adjuvant therapy, especially for poorly vascularized tumors that are less accessible to systemically administered drugs. In addition, micrometastases in different and distal regions of the lung could also be treated by precise instillation of chemotherapeutics in conjunction with drugs given systemically. Bronchiectasis—permanent enlargement of an airway—caused by a number of acquired or infective diseases (e.g., tuberculosis, pneumonia, and cystic fibrosis) can result in secluded regions of airway that harbor pathogens that are extremely difficult to clear with orally or systemically administered antibiotics. In such cases, liquid plug instillation could be used to deliver high concentrations of antibiotics directly to infected sites. The instillation of liquid microvolumes could provide localized delivery of drugs at precisely known volumes and concentrations into targeted regions of the lung to treat a wide range of lung diseases.

Figures 19A, 19B:
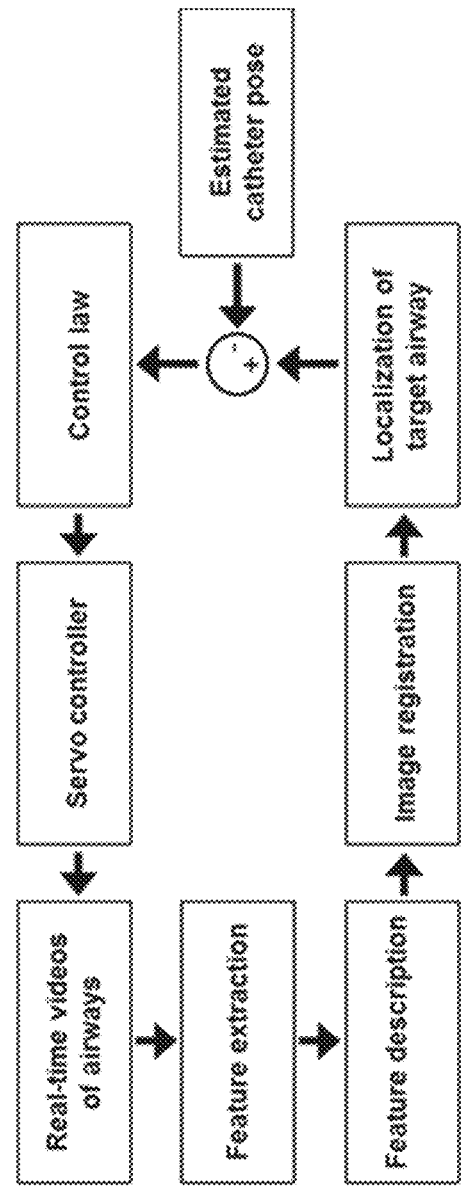
FIGS. 19A-19B show flow charts of maneuvering a steerable catheter using feature-based image registration and visual servo control methods.

FIGS. 19A-19B depict the maneuvering of a steerable catheter using feature-based image registration and visual servo control methods. In FIG. 19A, specific features of airways such as edges, corners, and areas are extracted from CT scan images using feature detection algorithms such as Scale-invariant feature transform (SIFT) or Speeded up robust features (SURF). In FIG. 19B, the pose of a steerable catheter is maneuvered via a servo controller based on the location of target airways determined through matching of corresponding features (i.e., image registration) in the pre-obtained images and the images collected from the live video during navigation. This image registration based navigation uses specific geometrical features of a target airway to enter determined from the three dimensional reconstructed airway model to direct the device in real-time through the navigation path in the patient. Features that can be used for airway recognition and registration include geometrical shapes of the entrance or near the airways seen at branches, distributions of blood vessel networks visible through the airway tissue, and textures and colors of the tissue. Feature extraction algorithms can be adapted from existing algorithms available through commercial software, such as MATLAB (Mathworks, Natick, Mass.). Geometrical features are continuously searched in a given image frame obtained from a live video during navigation, see FIGS. 19-22.

Figure 20:
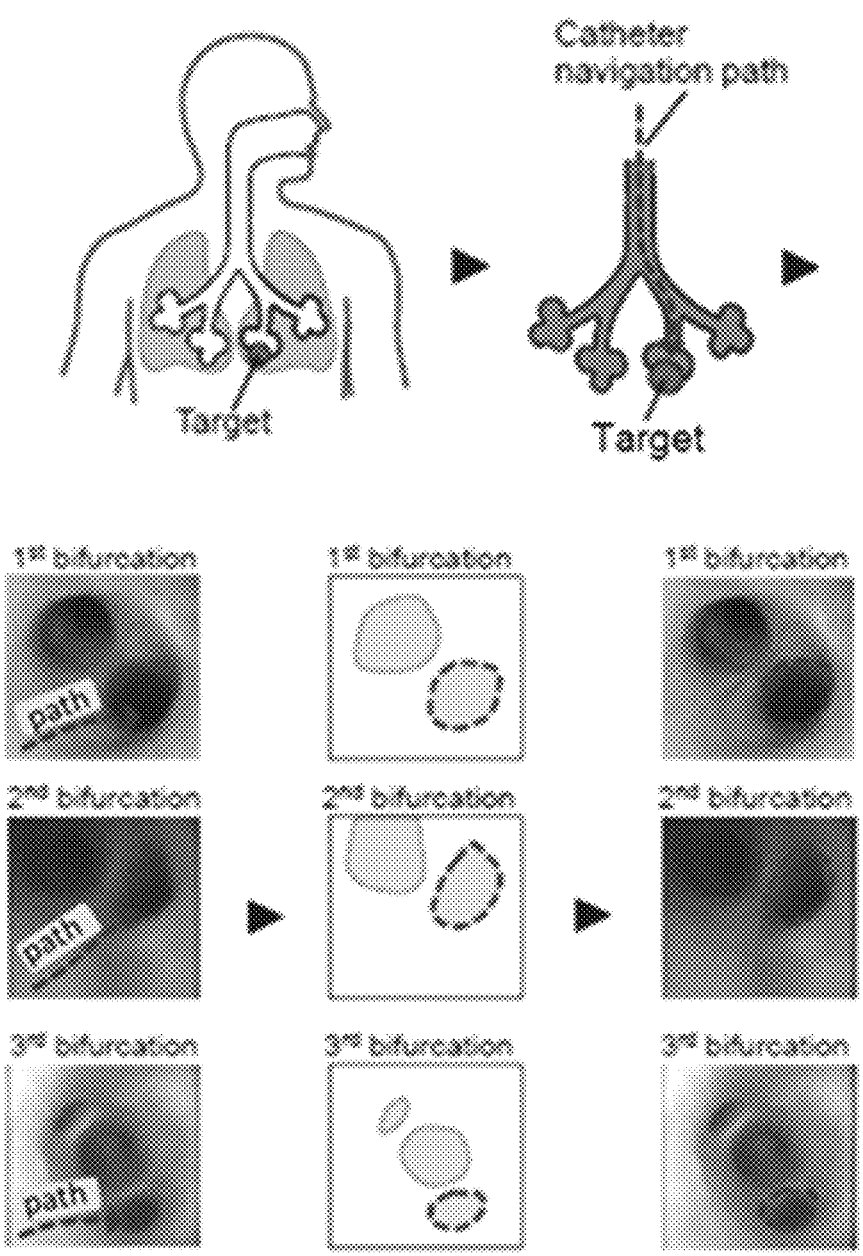
FIG. 20 shows schematic and photographic views of autonomous catheter navigation assisted with computer-vision based pattern recognition algorithm.

FIG. 20 shows catheter navigation assisted with pattern recognition algorithm. CT scan images of the patient's lung are obtained. The catheter navigation path to the target site is determined using a three dimensional reconstructed airway model obtained from the CT scan airway images. At airway bifurcations, the target airway branches to enter are identified from the three dimensional airway model. Specific features (e.g., geometrical shapes) of the airway branches to enter are extracted from the three dimensional reconstructed airway model using image processing techniques such as edge detection method. Using vision-based pattern recognition or feature matching algorithms, the airway features extracted are registered with images obtained real-time via the imaging probe of the catheter during navigation to facilitate computer-determined autonomous identification of target airways to enter at the bifurcation.

Figure 21:
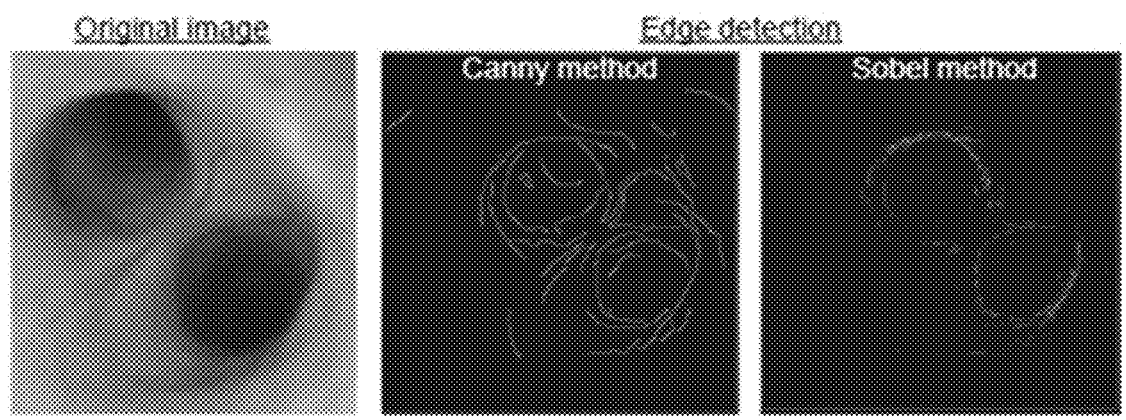
FIG. 21 shows images of extraction of airway features using edge detection methods.

FIG. 21 shows images of extraction of airway features using edge detection methods. FIG. 21 depicts an original image of airways at a bifurcation. Edges (or boundaries) of the airways were determined using image processing algorithms such as Canny and Sobel methods. Because each airway has a unique shape and geometry, these edges determined for can be used to identify target airways that the catheter would need to enter at bifurcations in the lung to get to the target site.

Figure 22:
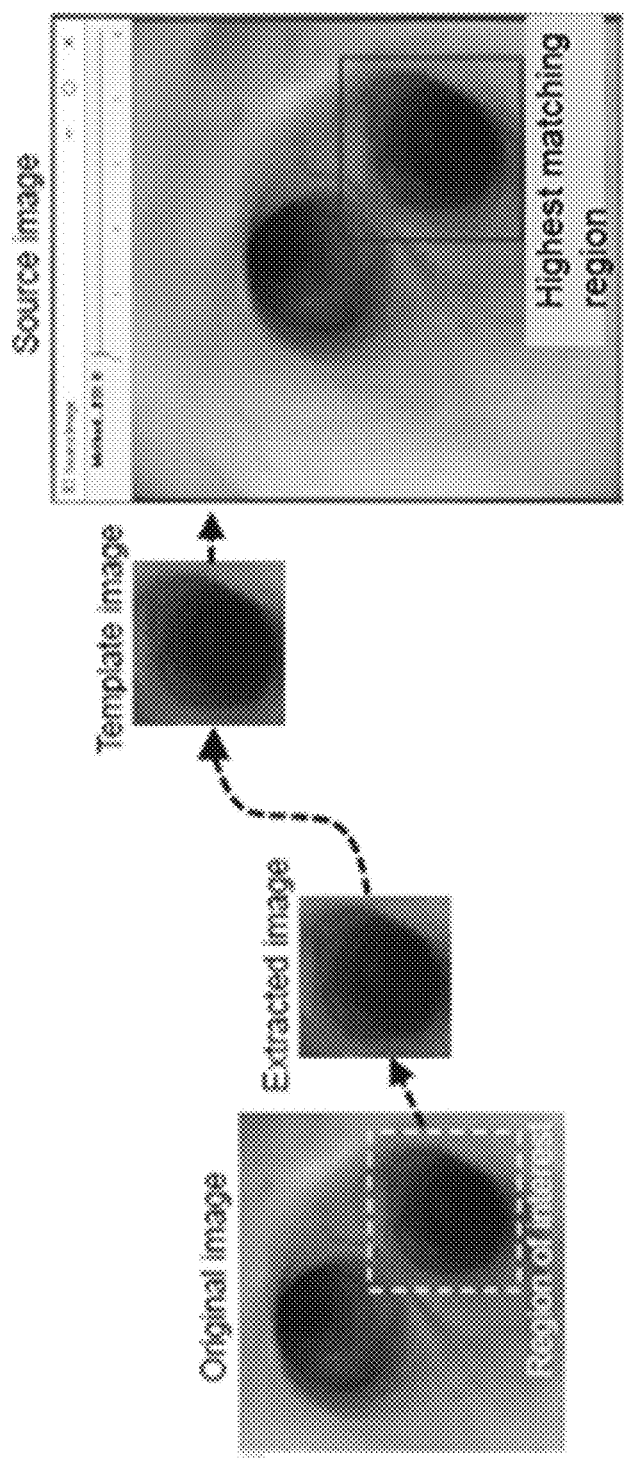
FIG. 22 shows images of pattern recognition demonstration using a feature matching algorithm.

FIG. 22 shows images of pattern recognition demonstration using a feature matching algorithm. In FIG. 22, a template image was extracted from the "original image" that contained "region of interest (ROI)". Here, as a proof of concept, ROI was the airway branch arbitrarily selected to which the steerable catheter would need to enter. The extracted image in FIG. 22 was used as a "template image" whose features were searched in the "source image" using a pattern-matching algorithm. Following the pattern matching process, a region that matches the most with the template image within the source image was identified and indicated with a red rectangular box. This computer-assisted airway pattern recognition can greatly enhance the accuracy of identifying the target airways realizing autonomous navigation toward the target regions in the lung.

Figure 23:
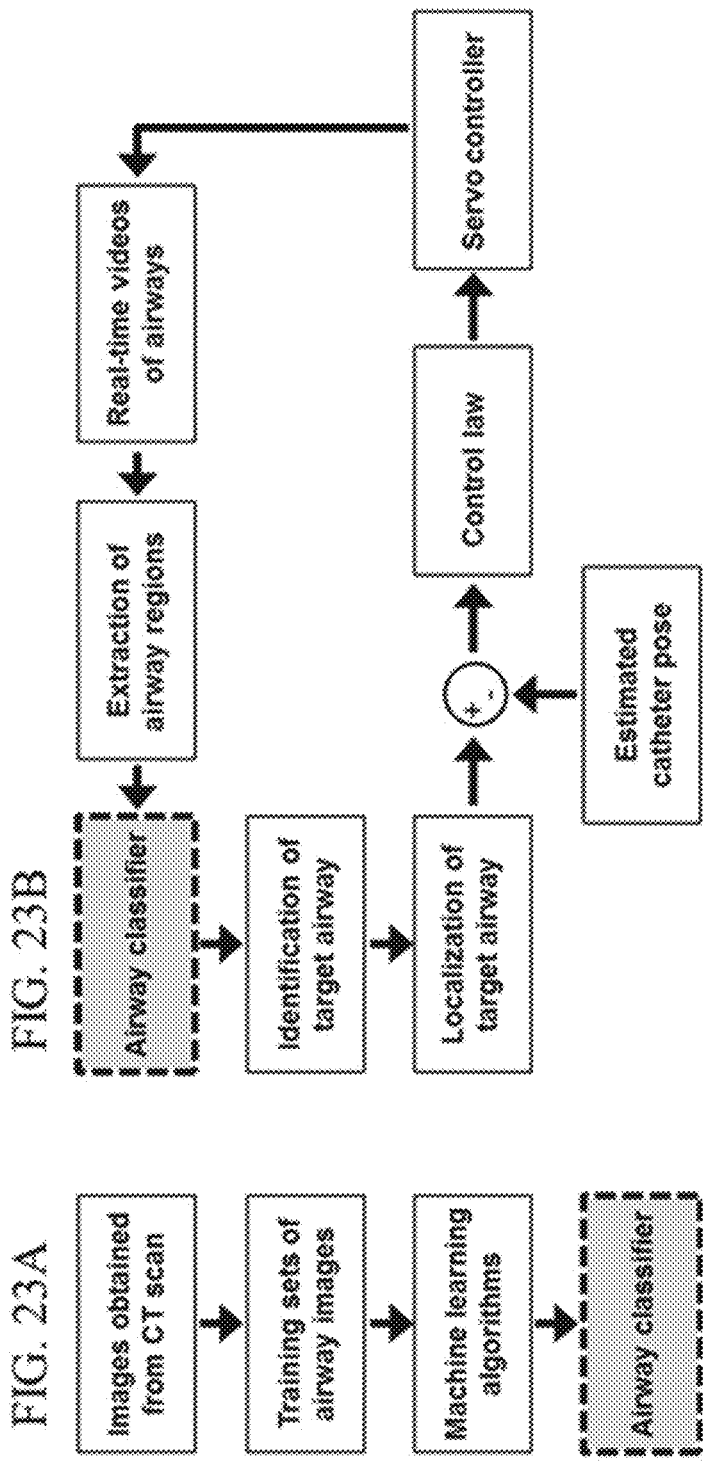
FIGS. 23A-23B show flow charts of maneuvering steerable catheter using machine learning and visual servo control algorithms.

FIGS. 23A-23B show flow charts of maneuvering a steerable catheter using machine learning and visual servo control algorithms. FIG. 23A depicts the use of machine learning algorithms (e.g., convolutional neural network) to generate an airway classifier from training sets of airway images. FIG. 23B depicts the maneuvering of the pose of a steerable catheter using a servo control algorithm (i.e., visual servoing), that maneuvering being based on the location and centers of target airways estimated using the airway classifier (dotted box) obtained in the schematic depicted in FIG. 23A.

Figure 24:
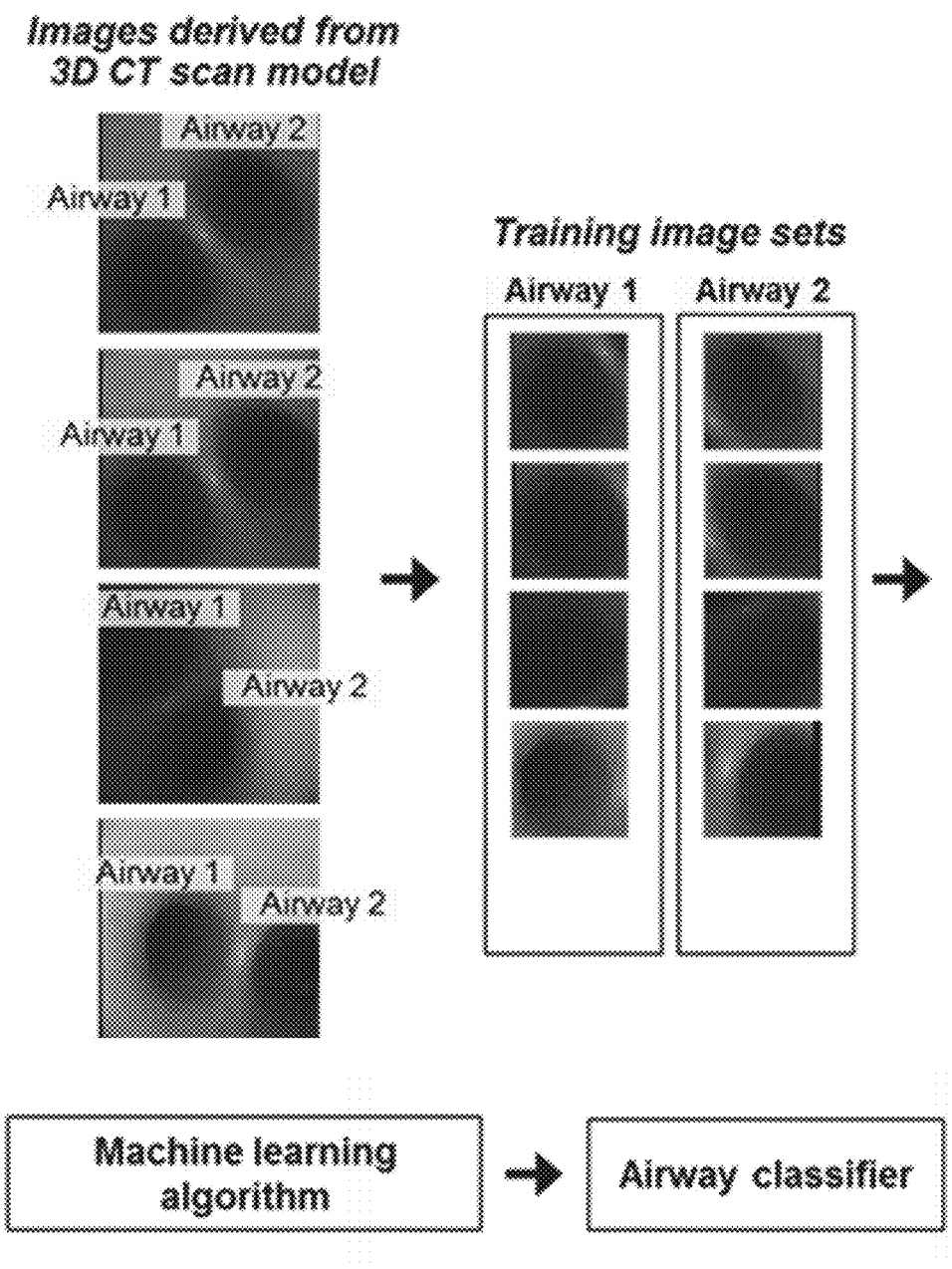
FIG. 24 shows generation of airway classifier using machine learning algorithms.

FIG. 24 depicts generation of an airway classifier using machine learning algorithms such as convolutional neural network. Two dimensional images of airways at a bifurcation are derived from the three dimensional airway model constructed from CT scan images. Airway regions are extracted from the images and grouped into each airway to produce sets of training images. For example, hundreds to thousands of two dimensional images derived from various viewing angles and differences of one airway branch of the three dimensional reconstructed airway model could be used in the extraction of airway regions to produce a set of training images. Using machine learning methods such as Convolutional Neural Networks, an airway classifier is generated. A dedicated airway classifier is generated for each airway bifurcation along the navigation path through which the catheter will pass as it navigates distally in the lung. In the neural-network based classification, input images (i.e., training images) are transformed through a network that consists of a series of layers such as convolutional layer, pooling layer, and fully connected layer. This network can learn representative features in raw input images and returns scores that are subsequently used for airway classification.

FIG. 25 shows use of airway classifier on unknown airways using machine learning algorithms. In a given image obtained at a bifurcation during navigation in real lung, airway regions (the darker regions enclosed by dotted rectangles in FIG. 25) are extracted using intensity threshold methods and tested through an airway classifier. Then, the airway classifier provides accurate classification of each unknown airway.

Figure 26A:
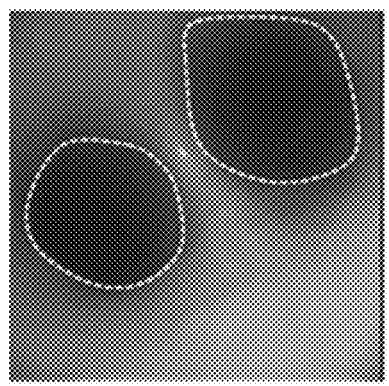
FIGS. 26A-26D show localization of airway centers.
Figure 26B:
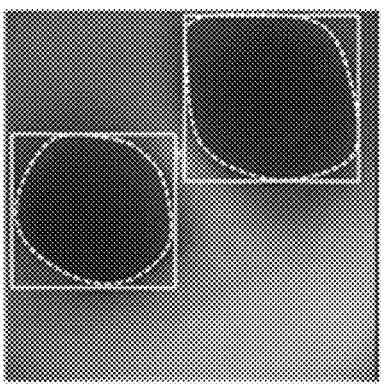
Figure 26C:
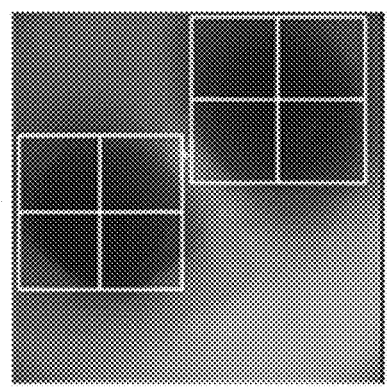
Figure 26D:
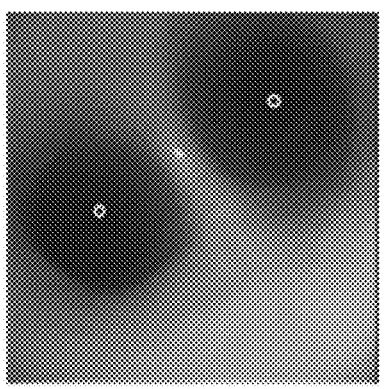

FIGS. 26A-26D show localization of airway centers. Airways normally appear darker than airway walls in an optical image. Thus, using a light-intensity thresholding technique, airway regions (dotted regions in FIG. 26A) can be selectively determined. Rectangles that enclose the dotted regions are obtained as shown in FIG. 26B. The center of each rectangle, which is identical to that of the corresponding airway, is determined through a simple calculation. FIG. 26C depicts one way to determine the center of the rectangle and FIG. 26D depicts the resulting airway center marked with an "o" at the center.

Figure 27:
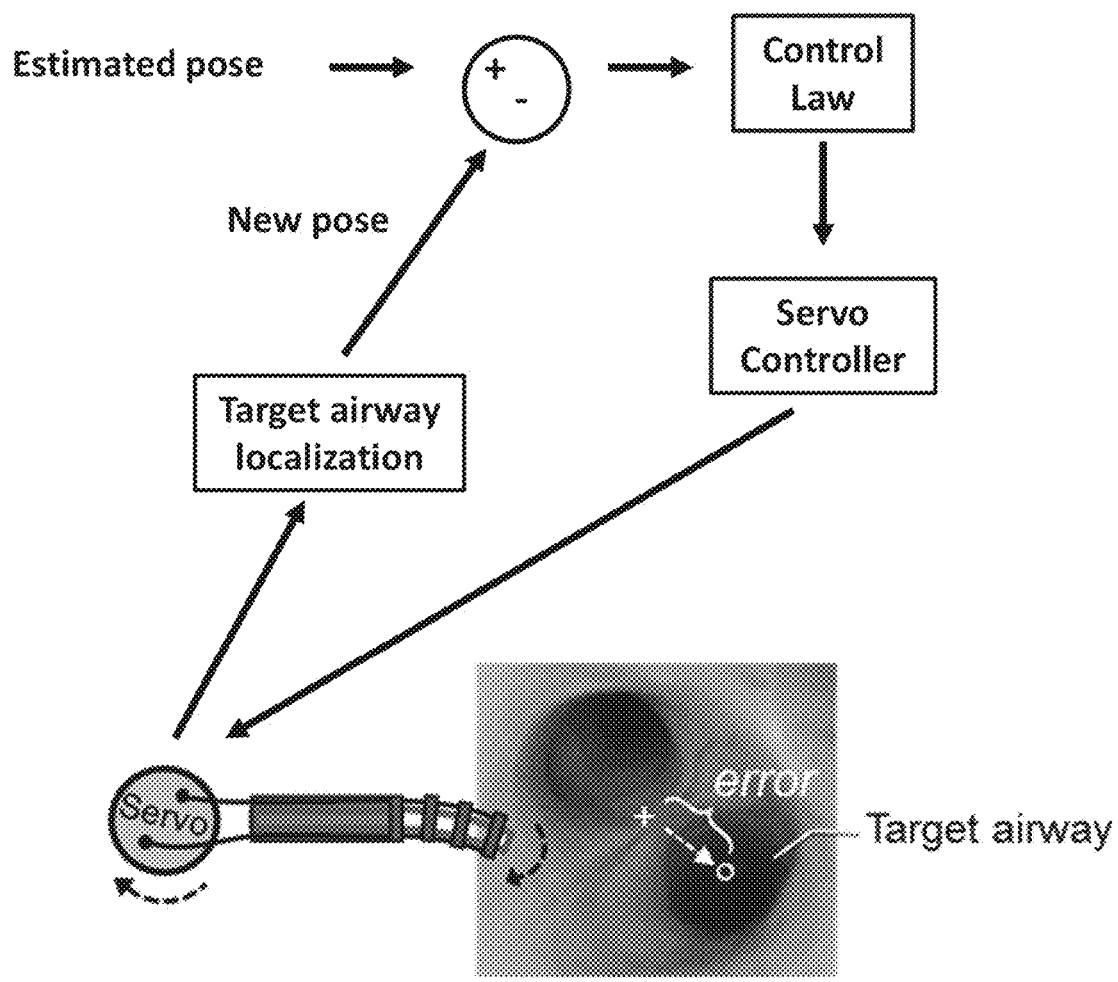
FIG. 27 shows catheter pose maneuvering using visual servoing technique.

FIG. 27 shows catheter pose maneuvering using visual servoing technique. For the device to enter a target airway at a bifurcation, the distal tip of the catheter is steered toward the center of the target airway center via servo controller. In FIG. 27, the "+" depicts the estimated pose of the distal tip of the catheter while the "o" depicts the center of the target airway. The device tip is continuously deflected until the distance ("error" in FIG. 27) between the image and target center becomes negligible. The location of the center of the target airway is determined via image processing and machine learning techniques as shown in FIGS. 26A-26D.

Figure 28A:
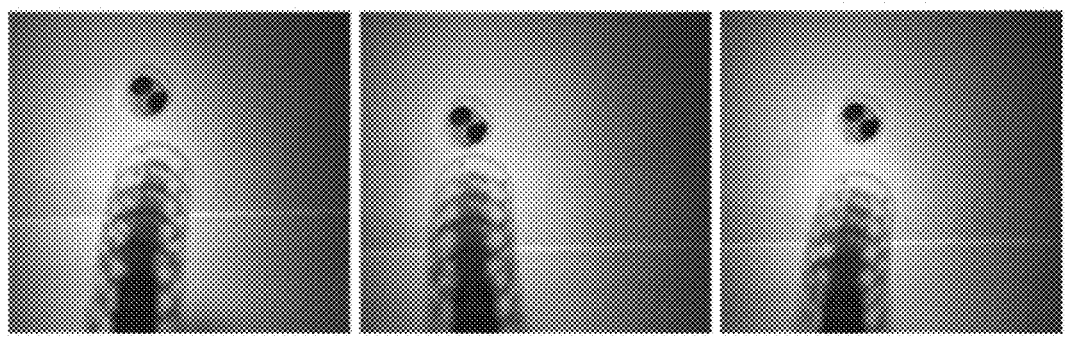
FIGS. 28A-28C show target airway detection and tracking via machine learning technology.
Figure 28B:
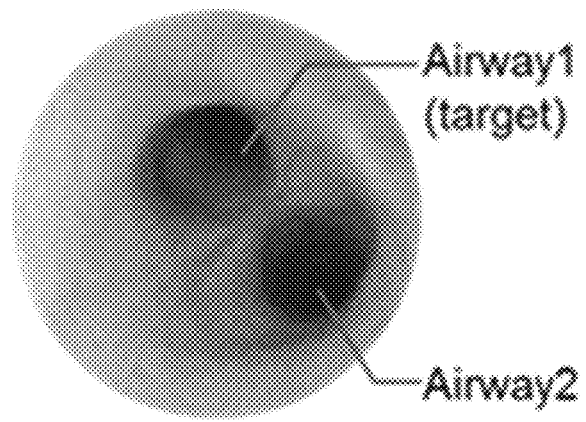
Figure 28C:
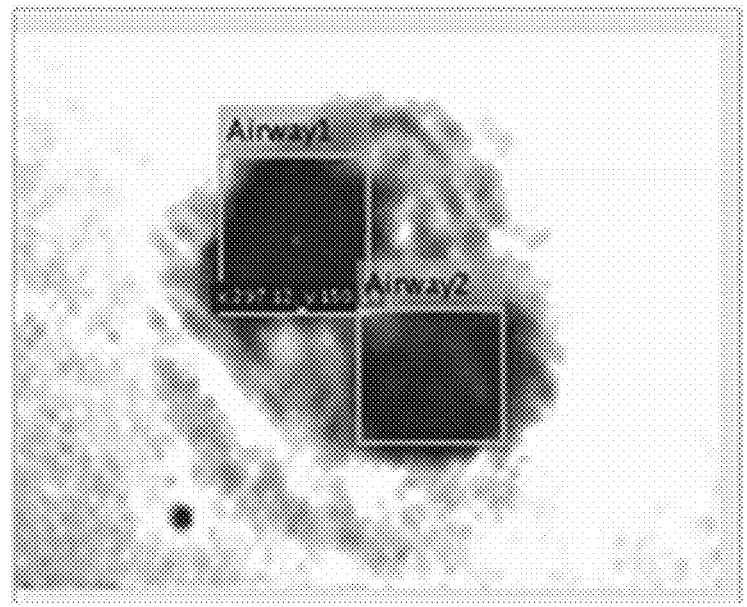

FIGS. 28A-28C depict target airway detection and tracking using machine learning. As shown in FIG. 28A, continuous detection and tracking of a target airway is achieved by maneuvering the deflection of the distal end of the steerable catheter using computer controlled servo motors. FIG. 28B represents an illustrative photograph of an airway bifurcation. FIG. 28C depicts the identification of Airway1 and Airway2 using machine learning.

Figure 29:
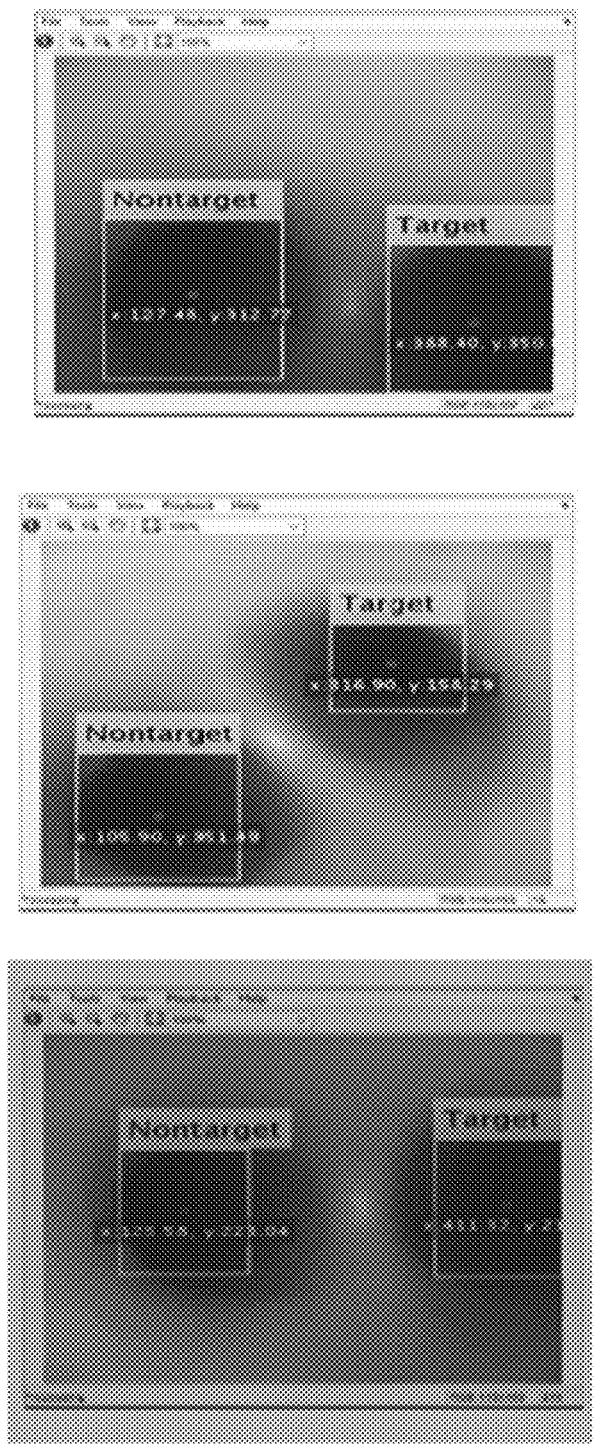
FIG. 29 shows identification of target and nontarget airways in real time using machine learning.

FIG. 29 shows identification of target and nontarget airways as well as their spatial locations in real time using machine learning.

Figure 30:
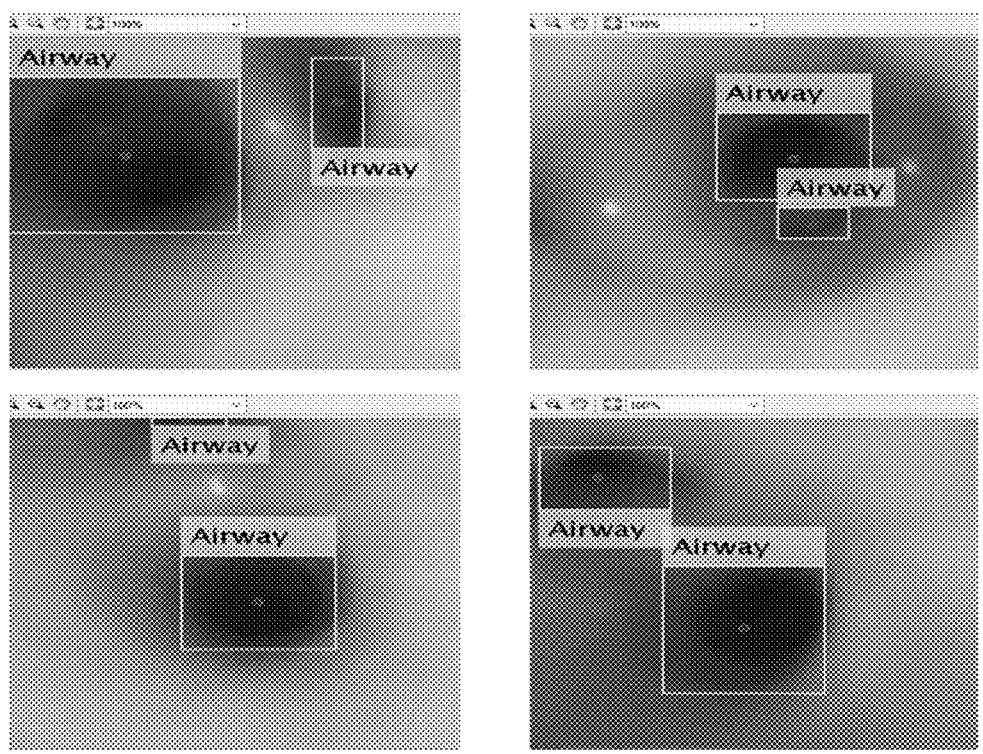
FIG. 30 shows detection of airways during navigation.

FIG. 30 shows detection of airways during navigation. The airways (darker regions of FIG. 30) and airway walls (brighter regions of FIG. 30) are detected during navigation using a machine vision technique.

The following examples illustrate various embodiments of the invention and are not limiting.

EXAMPLES

Targeted liquid film deposition was demonstrated in rat lungs by three different in vivo imaging modalities. Deposition of liquid film in the rat airway was experimentally verified using indocyanine green (ICG) fluorescent dye (excitation/emission: 785 nm/830 nm) in DI water visualized by near-infrared (NIR) imaging. Following instillation of a predefined liquid volume via a catheter in the rat trachea, the fluorescent signal was measured in situ on an open chest rat through the ventral surface of the lung. Dorsal imaging was done on explanted lungs. Liquid film deposition on alveolar surfaces was confirmed using fluorescent microbeads (1-μm diameter, excitation/emission: 580 nm/605 nm) using confocal imaging. The menisci of ICG plugs in the left main stem bronchus were visualized by NIR imaging.

Film Deposition in Target Regions of the Rat Lung

Figure 16:
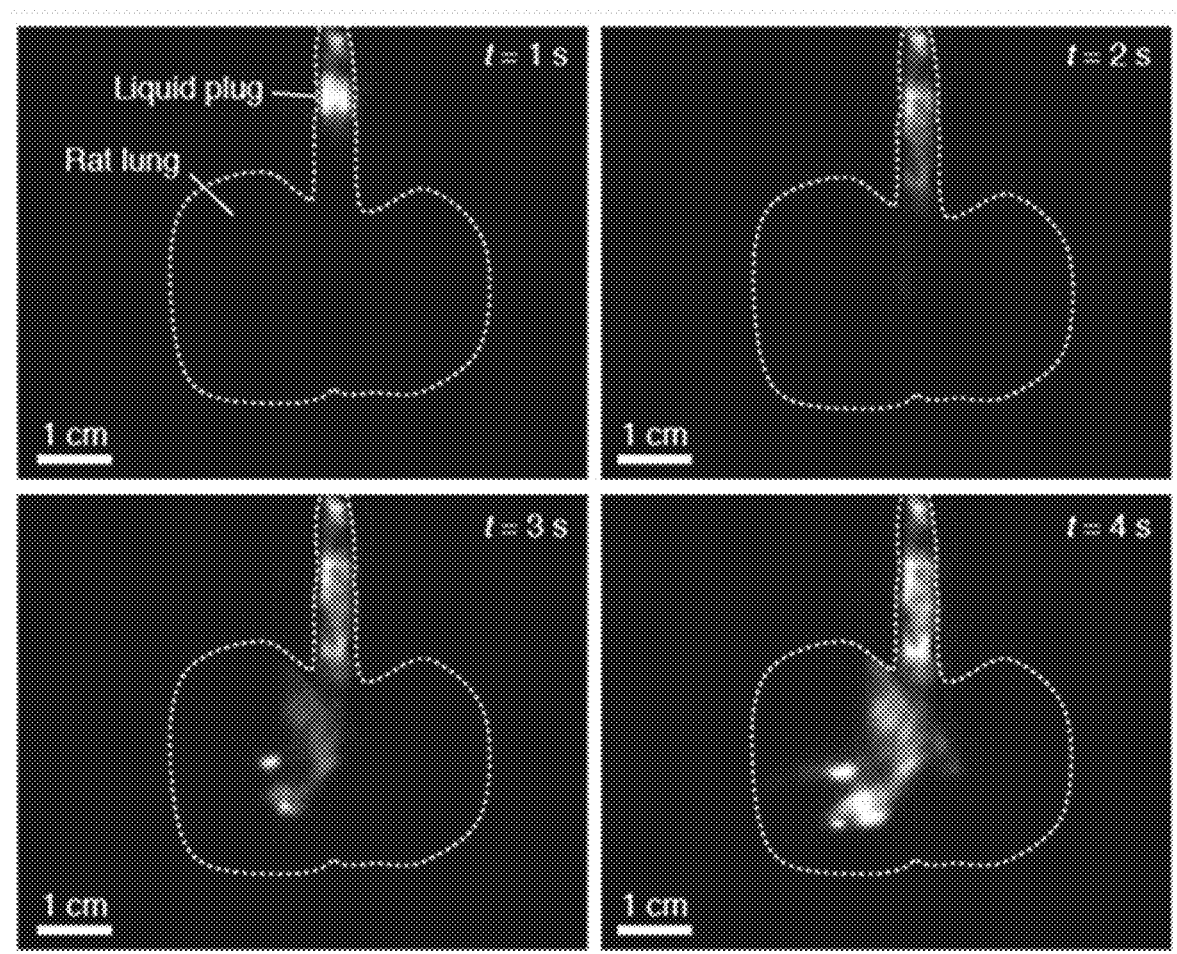
FIG. 16 shows images of liquid film deposition in rat upper airways by instillation of a liquid plug through the rat trachea.

Liquid film deposition in the rat upper airways was demonstrated by installation of an ICG liquid plug [surface tension σ of about 62 mN/m (22)] in the rat trachea. The liquid was instilled by infusing 4 mL of air for 4 s ($Ca_0=1.53\times10^{-3}$) through the trachea. FIG. 16 shows photographs of fluorescent imaging through the dorsal view of the rat pulmonary airway, showing progression of the liquid from the trachea into the upper airways at one-second intervals.

Figure 17:
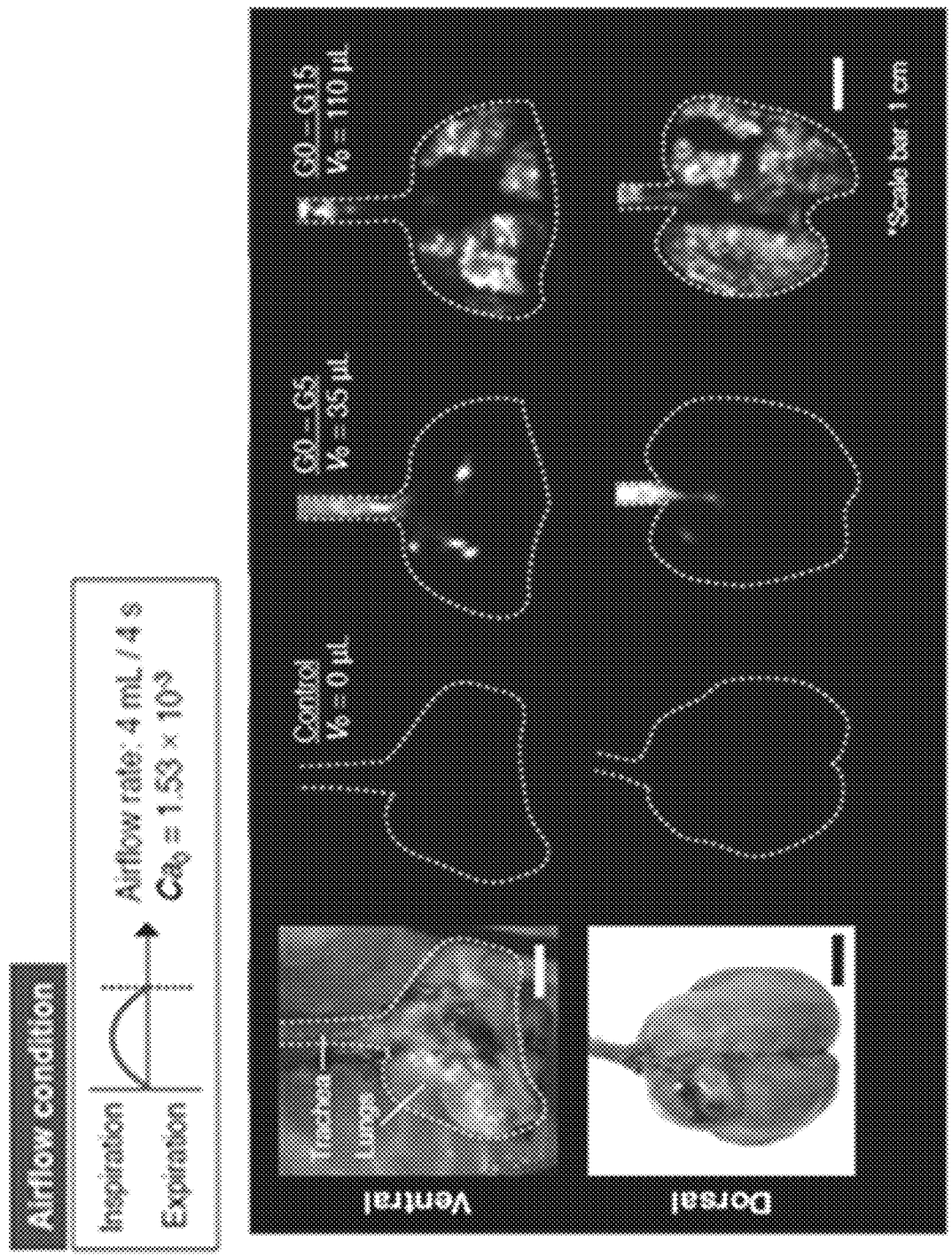
FIG. 17 shows images of liquid film deposition in selected regions of a rat lung.

Targeted delivery of liquid film into two different regions in the proximal airways is shown in FIG. 17. ICG liquid plugs [surface tension σ of about 62 mN/m (22)] with initial volumes $V_0$ of about 35 μL or 110 μL were instilled by infusing 4 mL of air for 4 s ($Ca_0=1.53\times10^{-3}$) for targeted film deposition within the large airways (target region: $G_0$-$G_5$) or into the small airways (target region: $G_0$-$G_{15}$), respectively. FIG. 17 shows photographs of brightfield and fluorescent images of the ventral and dorsal views of rat lungs. Control lungs that were not instilled with plugs displayed no fluorescence. In lungs instilled with 35-μL-volume plugs, the fluorescence signal showed that the length of the airways covered with film from the carina was about 1.3 cm, indicating that the plug traveled from $G_0$ to $G_5$ and deposited liquid film before it ruptured. Installation of 110-μL-volume plugs resulted in spatially uniform deposition throughout the lung, indicating penetration of liquid into smaller airways. Following instillation, lungs were ventilated, showed no regions of atelectasis, and recoiled without an increase in airflow resistance, suggesting negligible change in lung compliance and indicating that all plugs had ruptured and deposited liquid film in the airways.

Liquid Film Deposition from the Rat Trachea to the Distal Airways

Figure 18:
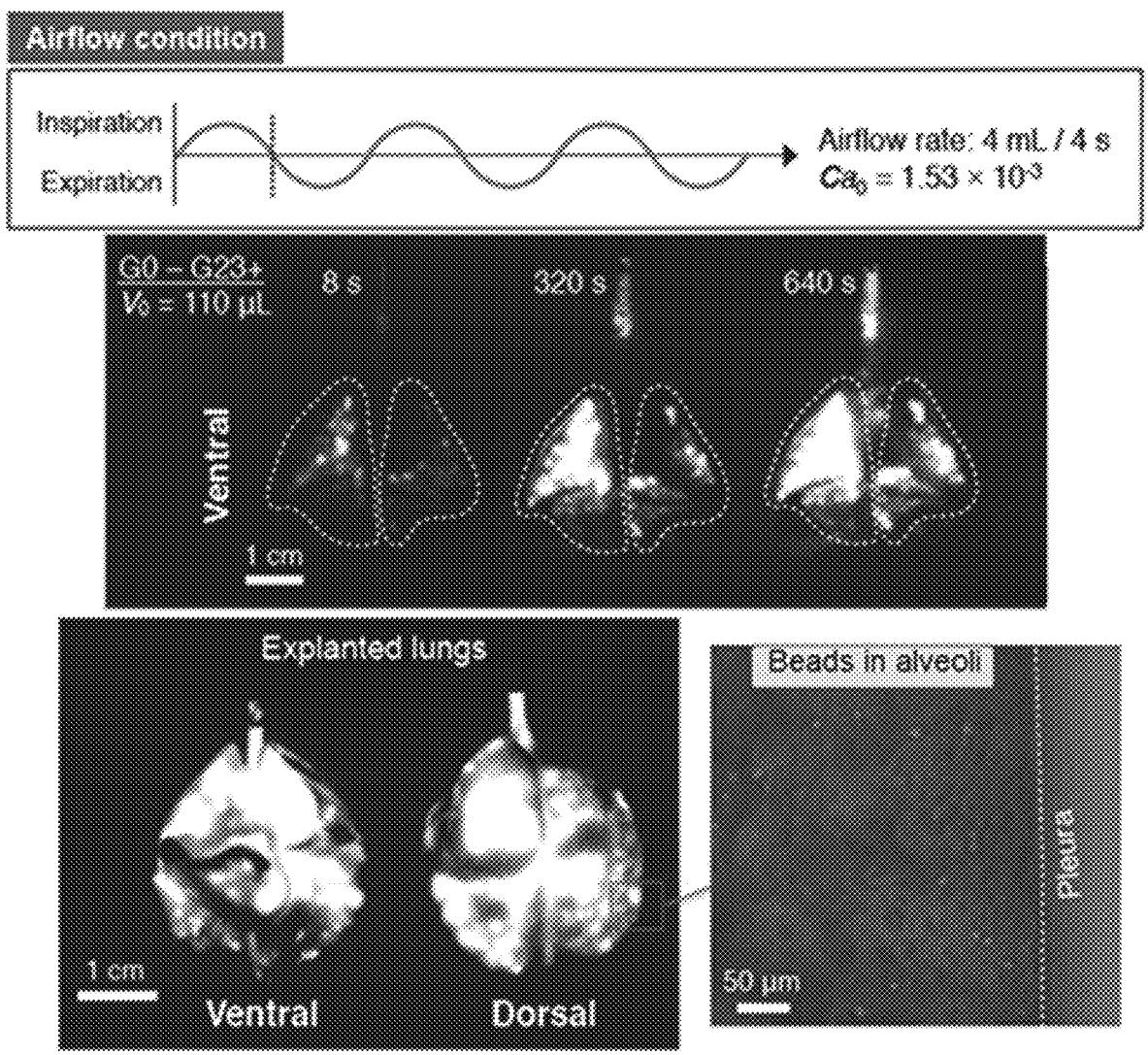
FIG. 18 shows images of liquid film deposition in alveoli of a rat lung.

Liquid film delivery from the rat trachea all of the way into the distal airways (target region: $G_0$-$G_{23+}$) was demonstrated by instilling 110-μL-volume liquid plugs followed by air ventilation at 1 mL/s. FIG. 18 shows fluorescent images of the course of film deposition at 8 s, 320 s and 640 s after instillation of the liquid plug. After the first cycle of air ventilation (8 s), fluorescence was visible throughout the lungs, confirming deposition of liquid film from the trachea into the deeper lung. When lungs were ventilated continuously, the fluorescence intensity increased as liquid advanced to the distal airways via repeated plug reformation and rupture until reaching the alveolar sacs. Because the ventral surface of the right upper lobe of the lung was perpendicular to the camera during the experiment, fluorescence change in that lobe was more apparent than in other parts of the lungs. As ventilation continued for about 10 minutes, the fluorescence intensity reached a maximum as the surfaces of alveolar sacs were coated with liquid film containing ICG.

Confirmation of Liquid Film Deposition in Target Airways

To more accurately determine the airways deposited with liquid film, liquid plugs containing carboxyfluorescein diacetate succinimidyl ester (CF SE) were used, which fluorescently labeled the airway epithelium in contact with the liquid film (FIG. 18). Fluorescent images of lung cross-sections showed that when 35 μL of CFSE solution was instilled, fluorescent signal indicating film deposited was observed only in the large airways ($G_0$-$G_5$). On the other hand, fluorescence was detected throughout the proximal airways ($G_0$-$G_{15}$) of the lungs instilled with 110 μL of CFSE. Although no signal was seen in the vast majority of alveoli, some peribronchiolar alveoli surrounding the target airways showed fluorescence due to diffusion of CFSE from the target airways. Furthermore, delivery of 110 μL of CFSE followed by 10 min ventilation resulted in film deposition in the entire airway surfaces ($G_0$-$G_{23+}$), as indicated by uniform fluorescence throughout the lungs. The presence of fluorescence beads in the subpleural region also verified film deposition into alveoli (FIG. 18). These results demonstrate that liquid film and small particles can be delivered to targeted generations of the lung by microvolume liquid instillation.

Having described and illustrated the principles of our invention with reference to the described embodiments, it will be recognized that the described embodiments can be modified in arrangement and detail without departing from such principles. It should be understood that the systems, processes, or methods described herein are not related or limited to any particular type of environment, unless indicated otherwise.

In view of the many possible embodiments to which the principles of our invention can be applied, we claim as our invention all such embodiments as can come within the scope and spirit of the following claims and equivalents thereto.

What is claimed is:

1. A method for targeted delivery of a liquid microvolume containing therapeutics into a lung, comprising
    positioning a steerable catheter device into a pulmonary airway of a lung, wherein the steerable catheter device comprises a distal section with a distal tip and an inner lumen;
    steering the distal section of the steerable catheter device to position the distal tip proximal to a desired locus within the pulmonary airway,
    instilling a liquid microvolume from the inner lumen of the steerable catheter device to an inner surface of the pulmonary airway;
    forming a plug of the liquid across a diameter of the pulmonary airway; and transporting the plug distally through the airway with air pressure delivered from the inner lumen of the elongated tubular member, thereby depositing a film comprising a portion of the liquid microvolume behind the plug.

2. The method of claim 1, wherein the therapeutic agent comprises at least one of drugs, biologics, nano-particulates, stem cell and gene therapies.

3. The method of claim 1, wherein steering the distal section of the steerable catheter device comprises steering the distal section of the steerable catheter device to position the distal tip proximal to the desired locus within the pulmonary airway using a navigation path determined from CT scan or MRI image.

4. The method of claim 3 wherein the navigation path is determined by obtaining CT scan images of a lung having a target site; and
    generating a three dimensional reconstructed airway model based on the CT scan images.

5. The method of claim 1, further comprising a computer-controlled robotic arm, and wherein steering the distal section of the steerable catheter device comprises utilizing the computer-controlled robotic arm to provide movement of the distal section of the elongated tubular member.

6. The method of claim 1, further comprising forming a secondary plug at a bifurcation within the pulmonary airway.

7. The method of claim 1, further comprising rupturing the plug by increasing air pressure delivered from the inner lumen of the elongated tubular member and extending the film comprising a portion of the liquid microvolume distally in the pulmonary airway.

8. The method of claim 1, further comprising reforming the plug of the liquid by applying reduced air pressure from the inner lumen of the elongated tubular member.

9. The method of claim 1, further comprising transporting liquid microvolume to distal regions of the lung by repeated cycles of forming a plug of the liquid across a diameter of the pulmonary airway;
- transporting the plug distally through the airway with air pressure delivered from the inner lumen of the elongated tubular member;
- rupturing the plug by increasing air pressure delivered from the inner lumen of the elongated tubular member; and
- reforming the plug of the liquid by applying reduced air pressure from the inner lumen of the elongated tubular member.

\* \* \* \* \*

UNITED STATES PATENT AND TRADEMARK OFFICE
CERTIFICATE OF CORRECTION

PATENT NO. : 11,738,175 B2
APPLICATION NO. : 16/546620
DATED : August 29, 2023
INVENTOR(S) : Gordana Vunjak-Novakovic et al.

It is certified that error appears in the above-identified patent and that said Letters Patent is hereby corrected as shown below:

In the Specification

In Column 1, immediately after the first paragraph, at Line 17, please add the following heading and Government Support Clause:
--STATEMENT OF GOVERNMENT SUPPORT
This invention was made with government support under EB027062 awarded by the National Institutes of Health. The government has certain rights in the invention.--

Signed and Sealed this
Fifth Day of March, 2024

Katherine Kelly Vidal
*Director of the United States Patent and Trademark Office*